United States Patent
Lacadie et al.

(10) Patent No.: US 7,064,139 B2
(45) Date of Patent: Jun. 20, 2006

(54) METHOD FOR TREATING RETROVIRAL INFECTIONS

(75) Inventors: John A. Lacadie, Woodbury, CT (US); James B. Pierce, Southbury, CT (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 377 days.

(21) Appl. No.: 10/021,453

(22) Filed: Oct. 29, 2001

(65) Prior Publication Data
US 2003/0139445 A1    Jul. 24, 2003

(51) Int. Cl.
*A61K 31/44* (2006.01)

(52) U.S. Cl. ..................................... 514/358; 514/345

(58) Field of Classification Search ................ 514/312, 514/311, 277, 279, 345, 358
See application file for complete search history.

(56) References Cited

U.S. PATENT DOCUMENTS 4,371,537 A * 2/1983 Markley et al. ............. 514/347
4,616,087 A * 10/1986 Wood ......................... 546/294

FOREIGN PATENT DOCUMENTS

GB           1 268 772      * 3/1972

\* cited by examiner

*Primary Examiner*—Shengjun Wang
(74) *Attorney, Agent, or Firm*—Daniel Reitenbach

(57) ABSTRACT

Compositions and methods of treating a retroviral infection in an afflicted host and/or inhibiting replication of a retrovirus involve administering a therapeutically effective amount of the following compound of formula I:

A-L-B                                            (I)

wherein A is a substituted or unsubstituted aryl compound, substituted or unsubstituted piperidyl, or substituted or unsubstituted thiopheneyl; L is sulfonyl, sulfinyl or thio; and B is a substituted or unsubstituted aromatic nitrogen containing heteroaryl compound; or pharmacologically acceptable acid-addition and base-addition salts thereof.

10 Claims, No Drawings

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
gctagaacgt atttgctgca gaacg                                25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 2
atccgaaaca actgtctgac tggca                                25

METHOD FOR TREATING RETROVIRAL INFECTIONS

FIELD OF THE INVENTION

This invention relates to methods for treating retroviral infections. More particularly, this invention relates to a method for the prevention or treatment of infection of a patient with HIV-1, HIV-2, human cytomegalovirus (HCMV) and human herpes virus type 6 (HHV-6) by administering an effective amount of pyridine or quinoline derivatives which inhibit replication of these retroviruses.

BACKGROUND OF THE INVENTION

There are currently about seven nucleoside reverse transcriptase (RT) inhibitors (NRTIs), about three nonnucleoside RT inhibitors (NNRTI) and about six protease inhibitors (PI) officially approved for the treatment of HIV-infected individuals. Reverse transcriptase and protease are virus-encoded enzymes. The clinical efficacy of the individual drugs varies depending on the nature and the molecular target of the drugs.

U.S. Pat. No. 5,268,389 describes certain thiocarboxylate ester compounds that are said to inhibit the replication of HIV. It is alleged that the selectivity of these compounds for HIV-1 is due to a highly specific interaction with HIV-1 RT.

U.S. Pat. No. 5,696,151 is directed to certain carbothioamides which inhibit replication of HIV-1 and reverse transcriptase mutants thereof.

The rapid emergence of HIV-1 strains resistant to several HIV-1-specific RT inhibitors in cell culture and in AIDS patients has caused concern for further development of these inhibitors in the clinic. See, e.g., Balzarini et al, J. Virology 67(9): 5353–5359 (1993) ("Balzarini I") and Balzarini et al, Virology 192: 246–253 (1993) ("Balzarini II").

Failure of long-term efficacy of known drugs can be associated with the appearance of dose-limiting and/or long-term side-effects, or more importantly, with the emergence of drug-resistant virus strains. Both RT inhibitors and protease inhibitors tend to select for virus strains that show a reduced susceptibility for the particular drugs. Moreover, a considerable cross-resistance exists between drugs that act against the same target.

Attempts have been made to combine various HIV-1 RT inhibitors to eliminate virus resistance. See, e.g., Balzarini I, supra. However, there is still a need for new compounds for the treatment of HIV, HCMV, HHV-6, and other retroviruses.

It is a purpose of this invention to provide compositions and methods of preventing or treating HIV-1, HIV-2, HCMV, or HHV-6 infections.

SUMMARY OF THE INVENTION

This invention relates to a method for treating a retroviral infection in an afflicted host which comprises administering to the host a therapeutically effective amount of the following compound of formula I:

A-L-B                     (I)

wherein component A is a substituted or unsubstituted aryl functional group, substituted or unsubstituted piperidyl, or substituted or unsubstituted thiopheneyl; component L is sulfonyl, sulfinyl or thio; and component B is a substituted or unsubstituted aromatic nitrogen containing heteroaryl functional group; as well as all pharmacologically acceptable acid-addition and base-addition salts thereof.

Examples of substituted or unsubstituted aryl functional groups suitable as component A would include those structures having formula II:

wherein Z is H, Cl, cyano, alkyl having from 1 to 15 carbon atoms, or alkoxyalkyl having 2 or 3 carbon atoms, Y is H or a double bond to a carbon which is attached to R, and R is phenyl, biphenyl, benzyl, polycycloaryl, heteroaryl or phenyl substituted with 1 to 5 substituents which may be the same or different selected from lower alkyl having from 1 to 5 carbon atoms, halogen, nitro, methoxy, ethoxy, benzyloxy, methylenedioxy, 2,2-dichlorocyclopropyl, trifluoromethyl, methylsulfonyl, cyano and phenoxy.

Examples of substituted or unsubstituted aromatic nitrogen containing heteroaryl functional groups suitable as component B include 4-methylquinolyl, 8-ethyl-4-methylquinolyl and those structures having formula III:

wherein n is 0 or 1, and $R_1$ and $R_2$ may be the same or different and are H, halogen, lower alkyl having from 1 to 4 carbon atoms, hydroxy, or nitro.

The compounds of this invention are useful for the inhibition of replication of retroviruses, e.g., HIV-1, HIV-2, HCMV, and HHV-6. The compounds of this invention are also useful for treating hosts infected with retroviruses, e.g., HIV-1, HIV-2, HCMV and HHV-6 in vitro and in vivo. The method is also useful in the therapeutic or prophylactic treatment of diseases caused by these retroviruses such as acquired immune deficiency syndrome (AIDS).

This invention additionally relates to a pharmaceutical composition comprising a therapeutically effective amount of a compound of formula I or a pharmacologically acceptable acid-addition or base-addition salt thereof and a pharmacologically acceptable carrier.

This invention also relates to a method of treating HIV, HCMV, and HHV-6 infection in an afflicted host which comprises administering to the host a therapeutically effective amount of the compound of Formula I.

DESCRIPTION OF THE INVENTION

Unless otherwise defined, the terms listed below are defined as follows:

"Alkyl" means straight, branched, or cyclic alkyl chains of 1 to 15 carbon atoms.

"Lower alkyl" means straight or branched alkyl chains of 1 to 5 carbon atoms.

"Halogenated alkyl" or "haloalkyl" means alkyl having 1 or more halo atoms, e.g., trifluoro-methyl, 2,2-dichloro cyclopropyl, etc.

"Heterocycloalkyl" means cyclic alkyl chain comprised of from 1 to 12 carbon atoms and 1 or more heteroatoms independently selected from the group consisting of N, O and S.

"Aryl" means an organic radical derived from an aromatic hydrocarbon by removal of one hydrogen, e.g., phenyl, biphenyl, and benzyl.

"Polycycloaryl" means an organic radical derived from an aromatic fused ring hydrocarbon by removal of one hydrogen, e.g., naphthyl and anthranyl.

"Heteroaryl" means a single ring or benzofused heteroaromatic group of 5 to 10 atoms comprised of 1 to 9 carbon atoms and 1 or more heteroatoms independently selected from the group consisting of N, O and S. N-oxides of the ring nitrogens are also included. Examples of single-ring heteroaryl groups are pyridyl, and thienyl. Examples of benzofused heteroaryl groups are quinolyl and isoquinolyl.

"Alkoxy" means an alkyl radical attached by an oxygen, i.e., alkoxy groups having 1 to 4 carbon atoms.

"Phenoxy" means a phenyl radical attached by an oxygen.

"Piperidyl" means an organic radical derived from piperidine by the removal of one hydrogen.

"Thiopheneyl" means an organic radical derived from thiophene by the removal of one hydrogen.

"Halogen", "halogenated" or "halo" refers to fluorine, chlorine, bromine or iodine radicals.

The compounds disclosed herein provide activity against retroviruses such as HIV, HCMV, and HHV-6. The use of such compounds, either alone or in combination with other pharmacologically active agents, provides highly desired new modalities for the treatment or prevention of HIV, HCMV and/or HHV-6.

This invention relates to a compound of the following formula I:

$$A\text{-}L\text{-}B \quad (I)$$

wherein component A is a substituted or unsubstituted aryl functional group, substituted or unsubstituted piperidyl, or substituted or unsubstituted thiopheneyl; component L is sulfonyl, sulfinyl or thio; and component B is a substituted or unsubstituted aromatic nitrogen containing heteroaryl functional group; as well as all pharmacologically acceptable acid-addition and base-addition salts thereof.

Examples of substituted or unsubstituted aryl functional groups suitable as component A include those structures having the following formula II:

(II)

wherein Z is H, Cl, cyano, alkyl having from 1 to 15 carbon atoms, or alkoxyalkyl having 2 or 3 carbon atoms; Y is H or a double bond to a carbon which is attached to R; and R is phenyl, biphenyl, benzyl, polycycloaryl, heteroaryl or phenyl substituted with 1 to 5 substituents which may be the same or different, the substituents being selected from the group consisting of lower alkyl having from 1 to 5 carbon atoms, halogen, nitro, methoxy, ethoxy, benzyloxy, methylenedioxy, 2,2-dichlorocyclopropyl, trifluoromethyl, methylsulfonyl, cyano and phenoxy.

Examples of substituted or unsubstituted aromatic nitrogen containing heteroaryl functional groups suitable as component B include 4-methylquinolyl, 8-ethyl-4-methylquinolyl and those structures having the following formula III:

(III)

wherein n is 0 or 1, and $R_1$ and $R_2$ may be the same or different and are H, halogen, lower alkyl having from 1 to 4 carbon atoms, hydroxy, or nitro.

Compounds of the invention may have at least one asymmetrical carbon atom and therefore all isomers, including diastereomers and rotational isomers are contemplated as being part of this invention. The invention includes (+)- and (−)- isomers in both pure form and in admixture, including racemic mixtures. Isomers can be prepared using conventional techniques, either by reacting optically pure or optically enriched starting materials or by separating isomers of a compound of formula I. Those skilled in the art will appreciate that for some compounds of formula I, one isomer may show greater pharmacological activity than other isomers.

Compounds of formula I can exist in unsolvated and solvated forms, including hydrated forms. In general, the solvated forms, with pharmaceutically acceptable solvents such as water, ethanol and the like, are equivalent to the unsolvated forms for purposes of this invention.

Compounds of the invention with a basic group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., compounds containing a carboxyl group. Acidic compounds according to the present invention can form pharmaceutically acceptable salts with inorganic and organic bases. Examples of such salts are the sodium, potassium, calcium, aluminum, lithium, gold and silver salts. Also included are salts formed with pharmaceutically acceptable amines such as ammonia, alkyl amines, hydroxyalkylamines, N-methlglucamine, and the like.

By way of non-limiting example, Table I below sets forth a number of antiretroviral compounds of the above formula I useful herein. The compounds of Table 1 are linked by the linkage group "L" at the substituted alkyl of "A" and the number 2 carbon of the heteroaryl functional group "B".

TABLE 1

| Compound No. | A | L | B |
| --- | --- | --- | --- |
| 1 | 1-(5-amino-2-methylphenyl)ethyl | 2-sulfonyl | Pyridine-N-oxide |
| 3 | 1-(2,5-dimethylphenyl)methyl | 2-sulfinyl | Pyridine-N-oxide |
| 4 | Phenylmethyl | 2-thio | Pyridine-N-oxide |
| 5 | Phenylmethyl | 2-sulfinyl | Pyridine-N-oxide |
| 6 | Phenylmethyl | 2-sulfonyl | Pyridine-N-oxide |
| 7 | 1-(2,5-dimethylphenyl)octyl | 2-sulfonyl | pyridine-N-oxide |
| 8 | 2-methyl-thiopheneyl | 2-sulfonyl | pyridine-N-oxide |
| 9 | 1-(2,5-dimethylphenyl)ethyl | 2-sulfonyl | pyridine-N-oxide |
| 10 | 1-(2,5-dimethylphenyl)methyl | 2-sulfonyl | pyridine-N-oxide |
| 11 | 1-(4-methylphenyl)methyl | 2-sulfonyl | pyridine-N-oxide |
| 12 | 1-(4-chlorophenyl)methyl | 2-sulfonyl | pyridine-N-oxide |
| 13 | 1-naphthylmethyl | 2-sulfonyl | pyridine-N-oxide |
| 14 | 1-(4-nitrophenyl)methyl | 2-sulfonyl | pyridine-N-oxide |
| 15 | 1-(2-chloropheny)lmethyl | 2-sulfonyl | pyridine-N-oxide |
| 16 | 1-(2-methylphenyl)methyl | 2-sulfonyl | pyridine-N-oxide |
| 17 | 1-(2,6-dichlorophenylmethyl | 2-sulfonyl | pyridine-N-oxide |
| 18 | 1-(2,4-dichlorophenyl)methyl | 2-sulfonyl | pyridine-N-oxide |
| 19 | 1-(4-methoxyphenyl)methyl | 2-sulfonyl | pyridine-N-oxide |
| 20 | 1-(2-methoxy-5-nitrophenyl)methyl | 2-sulfonyl | pyridine-N-oxide |
| 21 | 1-(2-chloro-4,5-dioxymethylenephenyl)methyl | 2-sulfonyl | pyridine-N-oxide |
| 22 | 1-(2-fluorophenyl)methyl | 2-sulfonyl | pyridine-N-oxide |
| 23 | 1-((4-methylsulfonyl-2'-pyridine-N-oxide)phenyl)methyl | 2-sulfonyl | pyridine-N-oxide |
| 24 | 1-(2-cyanophenyl)methyl | 2-sulfonyl | pyridine-N-oxide |
| 25 | 1-[((2,5-dimethyl)-4-methylsulfonyl-2'-pyridine-N-oxide]phenyl)methyl | 2-sulfonyl | pyridine-N-oxide |
| 27 | 1-(3-methyphenyl)methyl | 2-sulfonyl | pyridine-N-oxide |
| 28 | 1-(3-fluorophenyl)methyl | 2-sulfonyl | pyridine-N-oxide |
| 29 | 1-(4-fluorophenyl)methyl | 2-sulfonyl | pyridine-N-oxide |
| 30 | 1-(2-methoxy-5-methylphenyl)methyl | 2-sulfonyl | pyridine-N-oxide |
| 31 | 1-(2-bromo-5-methoxyphenyl)methyl | 2-sulfonyl | pyridine-N-oxide |
| 32 | 1-(2,3,4,5,6-pentachlorophenyl)methyl | 2-sulfonyl | pyridine-N-oxide |
| 33 | 1-(2,3,6-trichlorophenyl)methyl | 2-sulfonyl | pyridine-N-oxide |
| 34 | 1-(4-cyanophenyl)methyl | 2-sulfonyl | pyridine-N-oxide |
| 35 | 1-(2,5-bis-1'-methylethylphenyl)methyl | 2-sulfonyl | pyridine-N-oxide |
| 37 | 1-(3,4-dichlorophenyl)methyl | 2-sulfonyl | pyridine-N-oxide |
| 38 | 1-(3-bromophenyl)methyl | 2-sulfonyl | pyridine-N-oxide |
| 39 | 1-(3,4-dioxymethylenephenyl)methyl | 2-sulfonyl | pyridine-N-oxide |
| 40 | 1-(4-(2'-methylbutyl)phenyl)methyl | 2-sulfonyl | pyridine-N-oxide |
| 41 | 1-(2,3,6-trimethylphenyl)methyl | 2-sulfonyl | pyridine-N-oxide |
| 42 | 1-(2-nitrophenyl)methyl | 2-sulfonyl | pyridine-N-oxide |
| 43 | 1-(2-methylnaphthyl)methyl | 2-sulfonyl | pyridine-N-oxide |
| 44 | 1-(2-iodophenyl)methyl | 2-sulfonyl | pyridine-N-oxide |
| 45 | 1-(4-(2'-2'-dichlorocyclopropyl)phenyl)methyl | 2-sulfonyl | pyridine-N-oxide |
| 46 | 1-(3,4-dimethoxyphenyl)methyl | 2-sulfonyl | pyridine-N-oxide |
| 47 | 1-(2,5-dimethoxyphenyl)methyl | 2-sulfonyl | pyridine-N-oxide |
| 48 | 1-(2-ethoxyphenyl)methyl | 2-sulfonyl | pyridine-N-oxide |
| 49 | 1-(2,3,5,6-tetrachloro-4-methylphenyl)methyl | 2-sulfonyl | pyridine-N-oxide |
| 50 | 1-(3,4,5-trimethoxyphenyl)methyl | 2-sulfonyl | pyridine-N-oxide |
| 51 | 1-(9-anthryl)methyl | 2-sulfonyl | pyridine-N-oxide |
| 52 | 1-(2,4-dimethylphenyl)methyl | 2-sulfonyl | pyridine-N-oxide |
| 53 | 2-naphthylmethyl | 2-sulfonyl | pyridine-N-oxide |
| 54 | 1-1'-biphenyl-4yl-methyl | 2-sulfonyl | pyridine-N-oxide |
| 55 | 1-(4-(2'-methylpropyl)phenyl)methyl | 2-sulfonyl | Pyridine-N-oxide |
| 56 | 1-(2-phenoxyphenyl)methyl | 2-sulfonyl | pyridine-N-oxide |
| 58 | 1-(4-(2'-methylethyl)phenyl)methyl | 2-sulfonyl | pyridine-N-oxide |
| 59 | 1-(4-ethylphenyl)methyl | 2-sulfonyl | pyridine-N-oxide |
| 60 | ethyl-1-((4-carbonyl carbamate)phenyl)methyl | 2-sulfonyl | pyridine-N-oxide |
| 61 | 1-((3-methoxy-4-methoxyphenyl)phenyl)methyl | 2-sulfonyl | pyridine-N-oxide |
| 62 | 1-(2-nitro-5-methylphenyl)methyl | 2-sulfonyl | pyridine-N-oxide |
| 63 | 1-(2,5-bis(1'-methylethyl)-4-bromophenyl)methyl | 2-sulfonyl | pyridine-N-oxide |
| 64 | 1-(3-nitro-4-chlorophenyl)methyl | 2-sulfonyl | pyridine-N-oxide |
| 65 | 1-(3,5-dinitrophenyl)methyl | 2-sulfonyl | pyridine-N-oxide |
| 66 | 1-(3-methyl-4-nitrophenyl)methyl | 2-sulfonyl | pyridine-N-oxide |
| 67 | 1-(3-nitro-4-methylphenyl)methyl | 2-sulfonyl | pyridine-N-oxide |
| 69 | 1-(2-chloro-4-nitrophenyl)methyl | 2-sulfonyl | pyridine-N-oxide |
| 70 | 1-(2,5-dimethylphenyl)methyl | 2-sulfinyl | 3-methylpyridine-N-oxide |
| 71 | 1-(2,5-dimethylphenyl)ethyl | 2-sulfonyl | 3-methylpyridine-N-oxide |
| 72 | 1-(2,5-dimethylphenyl)methyl | 2-sulfonyl | 6-methylpyridine-N-oxide |
| 73 | 1-(2,5-dimethylphenyl)chloromethyl | 2-sulfonyl | 6-methylpyridine-N-oxide |
| 74 | 1-(2,5-dimethylphenyl)chloromethyl | 2-sulfonyl | 4-methylpyridine-N-oxide |
| 76 | 1-(2,5-dimethylphenyl)ethyl | 2-sulfonyl | 6-chloropyridine-N-oxide |
| 77 | 1-(2,5-dimethylphenyl)methyl | 2-sulfonyl | 6-chloropyridine-N-oxide |
| 78 | 1-(2,4-dimethylphenyl)ethyl | 2-sulfonyl | 3-methylpyridine-N-oxide |

TABLE 1-continued

| Compound No. | A | L | B |
|---|---|---|---|
| 79 | 1-(2,5-dimethylphenyl)propyl | 2-sulfonyl | 3-methylpyridine-N-oxide |
| 80 | phenylmethyl | 2-sulfonyl | 3-methylpyridine-N-oxide |
| 81 | 1-(2,5-dimethylphenyl)ethyl | 2-sulfonyl | 4,6-dimethylpyridine-N-oxide |
| 82 | 1-(2-methylphenyl)methyl | 2-sulfonyl | 3-methylpyridine-N-oxide |
| 83 | 1-(2,4-dimethylphenyl)methyl | 2-sulfonyl | 3-methylpyridine-N-oxide |
| 85 | 1-(3-trifluromethylphenyl)methyl | 2-sulfinyl | pyridine-N-oxide |
| 86 | 1-(4-methoxyphenyl)methyl | 2-sulfinyl | pyridine-N-oxide |
| 88 | 1-(2,4,6-trimethylphenyl)methyl | 2-sulfinyl | pyridine-N-oxide |
| 89 | 1-(3,4-dimethylphenyl)methyl | 2-sulfinyl | pyridine-N-oxide |
| 90 | 1-(2-methylphenyl)methyl | 2-sulfinyl | pyridine-N-oxide |
| 91 | 1-(4-methylphenyl)methyl | 2-sulfinyl | pyridine-N-oxide |
| 92 | 1-(4-fluorophenyl)methyl | 2-sulfinyl | pyridine-N-oxide |
| 93 | 1-(2-methoxy-5-methylphenyl)methyl | 2-thio | pyridine-N-oxide |
| 94 | 1-(2,5-dimethylphenyl)methyl | 2-sulfonyl | 5-chloropyridine-N-oxide |
| 95 | 1-(2,5-bis-2'-methylethylphenyl)methyl | 2-sulfinyl | pyridine-N-oxide |
| 96 | 1-(3,4-dioxymethylenephenyl)methyl | 2-sulfinyl | pyridine-N-oxide |
| 97 | 1-(2,3,6-trimethylphenyl)methyl | 2-sulfinyl | pyridine-N-oxide |
| 98 | 1-(3,4-dimethoxyphenyl)methyl | 2-sulfinyl | pyridine-N-oxide |
| 102 | 1-phenylethyl | 2-sulfinyl | pyridine-N-oxide |
| 103 | 1-(2,5-dimethylphenyl)ethyl | 2-sulfinyl | pyridine-N-oxide |
| 104 | 1-(2-methylphenyl)ethyl | 2-sulfonyl | pyridine-N-oxide |
| 105 | 1-chloromethylphenyl | 2-sulfonyl | pyridine-N-oxide |
| 106 | 1-(2,5-dimethylphenyl)chloromethyl | 2-sulfonyl | pyridine |
| 107 | 1-phenylethyl | 2-sulfonyl | 8-ethyl-4-methylquinolyl |
| 108 | 1-(2,5-dimethylphenyl)ethyl | 2-sulfonyl | 4-methylpyridine-N-oxide |
| 110 | 1-(2,5-dimethylphenyl)ethyl | 2-sulfonyl | 5-methylpyridine-N-oxide |
| 114 | 1-chloromethylphenyl | 2-sulfonyl | 5-chloropyridine-N-oxide |
| 115 | 1-phenylethyl | 2-sulfonyl | 3-methylpyridine-N-oxide |
| 117 | 1-(2-chlorophenyl)methyl | 2-sulfonyl | 3-methylpyridine-N-oxide |
| 118 | 1-(2-methyl-4-nitrophenyl)methyl | 2-sulfonyl | 3-methylpyridine-N-oxide |
| 120 | 1-(2-chlorophenyl)ethyl | 2-sulfonyl | 3-methylpyridine-N-oxide |
| 121 | 3-methyl-(1-2-methyl-3-nitrophenyl)ethyl | 2-sulfonyl | 3-methylpyridine-N-oxide |
| 123 | 1-(2,5-dimethylphenyl)methoxyethyl | 2-sulfonyl | pyridine |
| 124 | 1-(2,5-dimethylphenyl)ethyl | 2-sulfonyl | 3-chloropyridine-N-oxide |
| 125 | 1-(2,5-dimethylphenyl)chloromethyl | 2-sulfonyl | 3-chloropyridine-N-oxide |
| 128 | 1-(4-chlorophenyl)methyl | 2-sulfinyl | 4-methylpyridine-N-oxide |
| 129 | 1-(4-chlorophenyl)methyl | 2-sulfonyl | 4-methylpyridine-N-oxide |
| 132 | Phenylmethyl | 2-thio | 3-chloropyridine-N-oxide |
| 133 | 1-(2,5-dimethylphenyl)methyl | 2-thio | 3-chloropyridine-N-oxide |
| 134 | 1-(4-methoxyphenyl)methyl | 2-thio | 4-(2'-methylpropyl)pyridine-N-oxide |
| 135 | 1-(4-methoxyphenyl)methyl | 2-sulfonyl | 4-(2'-methylpropyl)pyridine-N-oxide |
| 136 | phenylmethyl | 2-sulfinyl | 3-chloropyridine-N-oxide |
| 137 | 1-(2,6-dichlorophenyl)methyl | 2-thio | 3-methylpyridine-N-oxide |
| 138 | 1-(2,6-dichlorophenyl)methyl | 2-sulfinyl | 3-methylpyridine-N-oxide |
| 139 | 1-(2,6-dichlorophenyl)methyl | 2-sulfonyl | 3-methylpyridine-N-oxide |
| 140 | Phenylmethyl | 2-thio | 3-hydroxypyridine |
| 142 | 1-(3-methylphenyl)methyl | 2-thio | N-methylpyridine hydrochloride |
| 143 | Phenylmethyl | 2-sulfonyl | pyridine |
| 146 | Phenylmethyl | 2-thio | 3-nitropyridine-N-oxide |
| 148 | 1-(2,5-dimethylphenyl)methyl | 2-thio | pyridine |
| 149 | Phenylmethyl | 2-thio | 6-chloropyridine-N-oxide |
| 150 | 1-(2,5-dimethylphenyl)methyl | 2-sulfonyl | pyridine |
| 151 | Phenylmethyl | 2-thio | 5-chloropyridine-N-oxide |
| 153 | 1-(2,5-dimethylphenyl)methyl | 2-sulfinyl | 5-chloropyridine-N-oxide |
| 156 | 2-methyl-N-methylpiperidyl | 2-thio | pyridine-N-oxide |
| 157 | 1-(2,5-dimethylphenyl)methyl | 2-thio | pyridine hydrochloride |
| 158 | 1-phenyl-b-cyanoethylene | 2-thio | pyridine-N-oxide |
| 159 | 1-(4-methoxyphenyl)-b-cyanoethylene | 2-thio | pyridine-N-oxide |
| 160 | 1-(3,4,5-trimethoxyphenyl)-b-cyanoethylene | 2-thio | pyridine-N-oxide |
| 161 | 1-(2,5-dimethylphenyl)ethyl | 2-sulfonyl | pyridine |
| 162 | 1-(2,5-dimethylphenyl)ethyl | 2-thio | 4-methylquinolyl |
| 163 | 1-(2,5-dimethylphenyl)ethyl | 2-sulfinyl | pyridine |
| 164 | 1-(2,5 dimethyl phenyl)methyl | 2-thio | 3-methylpyridine-N-oxide |
| 165 | 1-(2,5 dimethyl phenyl)methyl | 2-sulfonyl | 3-methylpyridine-N-oxide |

Compounds of formula I such as those listed above may be prepared by a variety of methods known to those skilled in the art. For example, U.S. Pat. Nos. 3,960,542, 4,019,893, 4,050,921, and 4,294,970 the contents of each being incorporated herein by reference, describe methods of preparing 2-thio-, 2-sulfinyl-, and/or 2-sulfonyl-pyridine N-oxide derivatives. The parent 2-thiopyridine N-oxides may be prepared, e.g., by two procedures: (1) the reaction of 2-chloropyridine N-oxide with the appropriate mercaptan in the presence of an acid acceptor such as an alkaline earth hydroxide; (2) reaction of the sodium salt of 2-mercaptopy ridine N-oxide with a suitable halide preferably of, but not limited to, the benzyl type. The yields of the two procedures are comparable.

An alternate and useful synthetic route involves the oxidation of an arylalkylthiopyridine prepared by methods well known to those skilled in the art. The oxidation involves the conversion of both the sulfur and nitrogen to their higher oxidative states in a single preparative step. In this case the products are sulfones as the sequence of oxidation proceeds from sulfide→sulfoxide→sulfone→sulfone N-oxide. The oxidant most generally employed, but not limited to, is 30–50% hydrogen peroxide in glacial acetic acid. In excess of three equivalents of peroxide is necessary.

The conversion of the aryl(heteroaryl)alkylthiopyridine-N-oxide to analogous sulfinyl or sulfonyl compound may be accomplished by employing one or two equivalents of an oxidizing agent selected from, but not necessarily limited to, hydrogen peroxide, peracetic acid, and the aromatic peroxy acids. The ratio of peroxide to substrate varies with the desired product.

The solvents employed may vary with the oxidant as described in the literature (Katritsky and Lagowski, Chemistry of the Heterocyclic N-Oxides, Academic Press, 1971). Glacial acetic acid and water are preferred when hydrogen peroxide is used and a nonpolar solvent such as chloroform is preferred for use with the aromatic peroxy acids. When water is employed as a solvent, a catalyst of the nature of a tungsten, vanadium, zirconium or molybdenum salt (U.S. Pat. Nos. 3,005,852, 3,006,962, and 3,006,963 and British Pat. No. 1,335,626; the contents of each being incorporated by reference herein) is generally used. Temperature and time are a function of the sulfide employed with the range varying from about 50° C. to reflux in the case of water and acetic acid to about 0° to about 60° C. with chloroform.

The synthesis of 2-(alpha-aryl-alpha-chloromethyl sulfonyl)pyridine-N-oxides is also known and described in U.S. Pat. No. 4,360,677 the contents of which are incorporated by reference herein. The types of starting materials generally employed in the preparation of these compounds are known to those skilled in the art. For example, these parent 2-aryl methylsulfonylpyridine-N-oxides may be prepared by methods described in U.S. Pat. No. 3,960,542. Their subsequent conversion to (alphachloromethylsulfonyl)pyridine-N-oxides may be carried out using a modification of a known procedure. (C. Y. Meyers, et al., J. Org. Chem., 91,7510 (1969); C. Y. Meyers, et al., Tetrahedron Lett., 1105 (1974); the contents of each being incorporated by reference herein.)

The solvent, N,N-dimethylformamide, is used without drying. Sodium hydroxide (97–98%) is freshly ground to a powder before use, care being taken to avoid prolonged exposure to moisture. Temperature may generally be maintained from about −5° to about +5° C., with reaction times between about 25 and about 35 min.

The synthesis of substituted pyridine N-oxide compounds is described, e.g., in U.S. Pat. No. 4,394,155 and foreign patent publication EP 36388, the contents of each being incorporated by reference herein. The substituted pyridine N-oxide compounds are generally prepared, e.g., by first preparing the appropriate thio compound. An essentially equimolar amount of an alkali metal alkoxide is added with stirring at room temperature under an atmosphere of nitrogen to the substituted or non-substituted benzylmercaptan dissolved in a suitable solvent (such as a $C_1$ to $C_4$ aliphatic alcohol, preferably methanol). The resulting solution is added slowly to a solution of a substituted pyridine N-oxide hydrochloride, which has been treated with an essentially equimolar amount of alkali metal alkoxide. The molar ratio of mercaptide anion to pyridine N-oxide is maintained at about 1, and stirring, nitrogen atmosphere and reaction at room temperature are also maintained throughout the complete reaction. After all the reactants have been combined, the reaction mixture is refluxed from about one to about six hours. The thio product which precipitates when the reaction mixture is poured into a large excess of ice water is filtered, washed several times with water, air dried and recrystallized from an alcohol such as wet ethanol.

The thio compound may be oxidized to the desired sulfinyl or sulfonyl compound by known means, e.g. the thio compound dissolved in excess chloroform is stirred into a chloroform solution of m-chloroperbenzoic acid at about −10° C. to about 10° C. The reaction vessel is stoppered and kept at about 0° C. for about 24 hr. The by-product, m-chlorobenzoic acid, is removed by filtration and the remaining chloroform solution washed thoroughly with aqueous sodium bicarbonate solution, then water. The chloroform solution is dried (e.g. with anhydrous magnesium sulfate) and the solvent evaporated. The final product may be recrystallized from a suitable solvent (e.g. lower alcohol).

The following Table 2 identifies certain compounds useful in the practice of the invention herein that have been described previously. All patents listed in Table 2 are incorporated herein by reference. All the patents listed below are U.S. patents with the exception of EP 36638 and Japanese Patent 57181059.

TABLE 2

| Compound No. | Described in Patent No. | See |
|---|---|---|
| 3 | 3960542 | Example 29 |
| 4 | 4050921 | Example 2 |
| 5 | 4050921 | Example 61 |
| 6 | 4050921 | Example 4 |
| 7 | 4294970 | Example III |
| 8 | 4050921 | Example 188 |
| 9 | 3960542 | Example 6 |
| 10 | 3960542 | Example 1 |
| 11 | 4050921 | Example 7 |
| 12 | 4050921 | Example 8 |
| 13 | 3960542 | Example 21 |
| 14 | 4050921 | Example 15 |
| 15 | 3960542 | Example 22 |
| 16 | 3960542 | Example 11 |
| 17 | 3960542 | Example 14 |
| 18 | 3960542 | Example 34 |
| 19 | 4019893 | Example 35 |
| 20 | 3960542 | Example 25 |
| 21 | 3960542 | Example 26 |
| 22 | 3960542 | Example 27 |
| 24 | 4050921 | Example 54 |
| 27 | 4050921 | Example 64 |
| 28 | 4050921 | Example 71 |
| 29 | 4050921 | Example 73 |
| 30 | 3960542 | Example 35 |
| 31 | 3960542 | Example 36 |
| 32 | 3960542 | Example 37 |
| 33 | 3960542 | Example 15 |
| 34 | 4019893 | Example 72 |
| 35 | 4019893 | Example 74 |
| 37 | 3960542 | Example 42 |
| 38 | 4050921 | Example 124 |
| 39 | 3960542 | Example 46 |
| 41 | 3960542 | Example 18 |
| 42 | 3960542 | Example 48 |
| 43 | 3960542 | Example 50 |
| 44 | 3960542 | Example 52 |
| 45 | 4050921 | Example 149 |
| 46 | 3960542 | Example 58 |
| 47 | 3960542 | Example 60 |
| 48 | 4050921 | Example 163 |
| 49 | 4050921 | Example 171 |

TABLE 2-continued

| Compound No. | Described in Patent No. | See |
|---|---|---|
| 50 | 4050921 | Example 184 |
| 52 | 4360677 | Starting material for Ex. 14 |
| 53 | 3960542 | Example 7 |
| 54 | 4360677 | Reactant in example 4 |
| 55 | 4360677 | Starting material for Ex. 27 |
| 56 | 4360677 | Starting material for Ex. 31 |
| 58 | 4360677 | Starting material for Ex. 34 |
| 59 | 4360677 | Starting material for Ex. 35 |
| 70 | 4394155 | Example 3 |
| 71 | 4394155 | Example 4 |
| 72 | EP36638 | Example 14 |
| 74 | 4394155 | Example 19 |
| 78 | 4394155 | Example 13 |
| 79 | 4394155 | Example 28 |
| 80 | 4394155 | Example 21 |
| 82 | 4394155 | Example 24 |
| 83 | 4394155 | Example 12 |
| 85 | 4050921 | Example 59 |
| 86 | 4050921 | Example 60 |
| 88 | 3960542 | Example 30 |
| 89 | 3960542 | Example 32 |
| 90 | 3960542 | Example 33 |
| 91 | 4050921 | Example 70 |
| 92 | 4050921 | Example 72 |
| 93 | 3960542 | Precursor of compound in 4120692 Ex. 88 |
| 94 | 4394155 | Example 25 |
| 95 | 4050921 | Example 102 |
| 96 | 3960542 | Example 45 |
| 97 | 3960542 | Example 8 |
| 98 | 3960542 | Example 57 |
| 102 | 4050921 | Example 189 |
| 103 | 4050921 | Example 190 |
| 105 | 4360677 | Example 1 |
| 108 | 4394155 | Example 7 |
| 110 | 4394155 | Example 6 |
| 114 | 4394155 | Example 5 |
| 115 | 4394155 | Example 22 |
| 117 | 4394155 | Example 14 |
| 118 | 4394155 | Example 16 |
| 120 | 4394155 | Example 15 |
| 121 | Japanese patent 57181059 | |
| 128 | 4394155 | Example 26 |
| 129 | 4394155 | Example 27 |
| 135 | 4394155 | Example 30 |
| 153 | 4394155 | Example 18 |
| 143 | J. B. Baudin et al. Bull Soc. Chim. Fr. (1993), 130(6), 856 F. Naomichi et al. Heterocycles (1986), 24(11)3019 | |
| 164 | J. Ag. Food Chem 32(3), 221(1984) | Text page 222 |
| 165 | J. Ag. Food Chem 32(3), 221(1984) | Table III cmpd 1 |

The present invention also relates to a pharmaceutical composition comprising a compound of formula I of this invention and a pharmaceutically acceptable carrier. The compounds of formula I can be administered in any conventional dosage form known to those skilled in the art. Pharmaceutical compositions containing the compounds of formula I can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like. All routes of administration are contemplated including, but not limited to, parenteral, transdermal, subcutaneous, intramuscular, nasal, sublingual, transmucosal, inhalation, rectal and topical.

Thus, appropriate unit forms of administration include oral forms such as tablets, capsules, powders, cachets, granules and solutions or suspensions, sublingual and buccal forms of administration, aerosols, implants, subcutaneous, intramuscular, intravenous, intranasal, intraoccular or rectal forms of administration.

When a solid composition is prepared in the form of tablets, e.g., a wetting agent such as sodium lauryl sulfate can be added to micronized or non-micronized compounds of formula I and mixed with a pharmaceutical vehicle such as silica, gelatine starch, lactose, magnesium stearate, talc, gum arabic or the like. The tablets can be coated with sucrose, various polymers, or other appropriate substances. Tablets can be treated so as to have a prolonged or delayed activity and so as to release a predetermined amount of active compound continuously or at predetermined intervals, e.g., by using ionic resins and the like.

A preparation in the form of gelatin capsules may be obtained, e.g., by mixing the active principle with a diluent, such as a glycol or a glycerol ester, and incorporating the resulting mixture into soft or hard gelatin capsules.

A preparation in the form of a syrup or elixir can contain the active principle together, e.g., with a sweetener, methylparaben and propylparaben as antiseptics, flavoring agents and an appropriate color.

Water-dispersible powders or granules can contain the active principle mixed, e.g., with dispersants, wetting agents or suspending agents, such as polyvinylpyrrolidone, as well as with sweeteners and/or other flavoring agents.

Rectal administration may be provided by using suppositories which may be prepared, e.g., with binders melting at the rectal temperature, for example cocoa butter or polyethylene glycols.

Parenteral, intranasal or intraocular administration may be provided by using, e.g., aqueous suspensions, isotonic saline solutions or sterile and injectable solutions containing pharmacologically compatible dispersants and/or solubilizers, for example, propylene glycol or polyethylene glycol.

Thus, to prepare an aqueous solution for intravenous injection, it is possible to use a co-solvent, e.g., an alcohol such as ethanol, or a glycol such as polyethylene glycol or propylene glycol, and a hydrophilic surfactant such as Tween® 80. An oily solution injectable intramuscularly can be prepared, e.g., by solubilizing the active principle with a triglyceride or a glycerol ester.

Topical administration can be provided by using, e.g., creams, ointments or gels.

Transdermal administration can be provided by using patches in the form of a multilaminate, or with a reservoir, containing the active principle and an appropriate solvent.

Administration by inhalation can be provided by using, e.g., an aerosol containing sorbitan trioleate or oleic acid, for example, together with trichlorofluoromethane, dichlorofluoromethane, dichlorotetrafluoroethane or any other biologically compatible propellant gas; it is also possible to use a system containing the active principle, by itself or associated with an excipient, in powder form.

The active principle can also be formulated as microcapsules or microspheres, e.g., liposomes, optionally with one or more carriers or additives.

Implants are among the prolonged release forms which can be used in the case of chronic treatments. They can be prepared in the form of an oily suspension or in the form of a suspension of microspheres in an isotonic medium.

The daily dose of a compound of formula I for treatment of a disease or condition cited above is typically about 0.001 to about 100 mg/kg of body weight per day, preferably about 0.001 to about 10 mg/kg. For an average body weight of 70 kg, the dosage level may therefore range from about 0.1 to about 700 mg of drug per day, given in a single dose or 2–4 divided doses. It is contemplated that any range of the aforementioned doses may be administered at intervals greater than daily, e.g., one to four times per week over a period of several weeks or for greater periods. The exact dose, however, is determined by the attending clinician and is dependent on the potency of the compound administered, the age, weight, condition and response of the patient.

The therapeutically effective amount of the compounds of this invention that can be combined with the pharmacologically acceptable carrier to produce a single dosage form will vary depending upon the age and condition of the host treated and the particular mode of administration. In general, the compounds of this invention are most desirably administered at a concentration level that will generally afford antiretrovirally effective results without causing any medically unaccceptable harmful or deleterious side effects.

While the compounds of this invention can be administered as the sole active pharmaceutical agents, the compounds can also be used in combination with one or more other pharmaceutical agents which are not deleterious to the activity of the compounds of this invention or whose combination with the compounds will not have a deleterious effect on the host treated. Indeed, it is also contemplated that compounds of this invention may be combined with other antiviral agents or other agents useful in the treatment of conditions resulting from viral infection.

The following examples are provided to illustrate synthesis of certain compounds according to the present invention. These examples are included for purposes of illustration and are not intended to limit the invention herein in any way whatsoever.

EXAMPLE 1

Preparation of 2-[1-(2,5-Dimethylphenyl)octyl sulfonyl]pyridine N-oxide (Compound 7)

To a solution of 34.3 gm (0.1 mol) 2-[1-(2,5-dimethylphenyl) octylthio]pyridine N-oxide and 10.7 gm (0.26 mol) acetonitrile in 400 ml of methanol was added sufficient NaOH solution (6 N to minimize water) to adjust the pH in the operating range of 9.0 to 9.5 (true), approximately 11–12 (meter). 17 gm (0.26 mol) of 50% hydrogen peroxide was added in increments.

The reaction mixture was stirred in excess of 4 hours after peroxide addition. Quenching, filtering and washing yielded 27 gm of product melting at 134°–136° C.

EXAMPLE 2

Preparation of 2-(1-[2,5-Dimethylphenyl]ethylsulfonyl)pyridine N-oxide (Compound 9)

The intermediate 2-(1-[2,5-dimethylphenyl]-ethylthio) pyridine N-oxide is prepared from 1-(2,5-dimethylphenyl) ethyl chloride and 2-mercaptopyridine N-oxide, sodium salt by the procedure described in U.S. Pat. No. 3,960,542, Example 2. Melting point 118°–120° C. Structure confirmed by IR and NMR.

The thio compound (0.05 mole) is oxidized with MCPBA (0.1 mole) and isolated in the manner described in U.S. Pat. No. 3,960,542, Example 2. Yield 83% theory. Melting point 160°–163° C. (IR NO 1275 cm$^{-1}$, SO$_2$ 1315, 1145 cm$^{-1}$).

EXAMPLE 3

Preparation of 2-(2,5-Dimethylphenylmethylsulfonyl)pyridine N-oxide (Compound 10)

To a stirred solution of 792 gms (2.2 mole) (40% aqueous solution) 2-mercaptopyridine N-oxide, sodium salt in 1400 ml of ethanol is added 344 gms (2.2 mole) 2,5-dimethyl-benzylchloride over a period of 15 minutes. The mixture is brought to reflux for 15 minutes, filtered hot, and treated with 5 liters of cold water. The product is filtered off and oven dried to 533 gms of 2-(2,5-dimethylphenylmethylthio) pyridine N-oxide. Yield 97%. Melting point 140°–142° C.

To a vigorously stirred solution of 74 gms (0.3 mole) of the thio compound in 250 ml of glacial acetic acid at 45°–50° C. is added 75 ml of 30% hydrogen peroxide over a period of 15 minutes. The temperature is raised to 70° C. and after 30 minutes increased again to 80°–90° and held for 3 hours. The reaction mixture is lowered to ambient temperature and added slowly to two to three times its volume of vigorously agitated cold water. The pale yellow solid separates and is filtered off. Recrystallization from ethanol yields 74.5 gms of fine crystals melting at 156°–158° C. (IR NO 1275 cm$^{-1}$, SO$_2$ 1140, 1315 cm$^{-1}$). Yield 89% theory.

Analysis: Calc. For C$_{15}$NO$_3$S. C, 60.63; H, 5.45; N, 5.05; S. 11.54. Found: C, 60.66; H, 5.56; N, 5.18; S, 11.81.

To a heated (80°–90° C.) vigorously stirred slurry of 30 gms (0.12 mole of thio compound in 150 ml of water containing 10 gms of acetic acid and 0.2 gms of sodium tungstate dihydrate is slowly added 26 ml of 30% hydrogen peroxide. The addition is exothermic and the temperature is maintained at 80°–90° C. for the first 14 ml then allowing it to rise to the 95°–105° C. range for the remaining 12 ml.

The initial slurry becomes quite thin at the sulfoxide stage and again separating at the sulfone stage. Overall reaction time is about one hour. The reaction mixture is filtered, washed with water and air dried. Melting point (m.p.) 156°–158° C. Mixed m.p. with authentic sample shows no depression. Yield 32.8 gms (quantitative).

EXAMPLE 4

Preparation of 2-(2-Methylphenylmethylsulfonyl)-pyridine N-oxide (Compound 16)

The intermediate 2-(2-methylphenylmethylthio)-pyridine N-oxide is prepared by the procedure described in U.S. Pat. No. 3,960,542, Example 2 from α-chloro o-xylene and 2-mercaptopyridine N-oxide sodium salt. Melting point 134°–136° C. Yield 85% theory. Structure confirmed by IR and NMR.

A slurry of 14 gms (0.06 mole) thio compound, 100 ml water, 0.5 gms sodium tungstate dihydrate, and 4 ml of glacial acetic acid is heated to 75° C. Twelve ml hydrogen peroxide (30%) (0.12 mole) is added portionwise and with only a slight exotherm until 6 ml is consumed. The remaining 6 ml is added at steam bath temperature in three 2 ml portions at a rate controlled by testing the mixture with potassium iodide-starch paper to assure consumption of the previous peroxide. The final temperature was 97° C. after one hour. Cool, filter and wash cake with water and a small amount of cold ethanol. After drying the product 15.4 gms (99% theory) is obtained. Melting point 159°–160.5° C. Structure confirmed by IR.

Analysis: Calc. For $C_{13}H_{13}NO_3S$. C, 59.31; H, 4.98; N, 5.32. Found C, 59.30; H, 5.21; N, 5.31.

EXAMPLE 5

Preparation of
2-(2,6-Dichlorophenylmethylsulfonyl)pyridine
N-oxide (Compound 17)

A mixture of 37 gms (0.1 mole) of (40% solution) 2-mercaptopyridine N-oxide, sodium salt and 19.5 gms (0.1 mole) 2,6-dichlorobenzylchloride in 200 ml ethanol is warmed to 65° C. for thirty minutes, cooled and filtered. The filter cake is washed thoroughly with water and finally with 40 ml of acetone. Vacuum drying of the cake yields 25.3 gms (92% theory) of product, 2-(2,6-dichlorophenylmethylthio)pyridine N-oxide. Melting point 240°–241° C. Structure confirmed by IR.

A slurry of 29 gms (0.1 mole) of the thio compound in 300 ml of chloroform at 10° C. is treated slowly with 40 gms (0.2 mole) MCPBA (85%) in 450 ml of chloroform. The mixture is permitted to rise to ambient temperature resulting in a clear solution that is held sixteen hours. The solution is washed with saturated sodium bicarbonate solution, dried over magnesium sulfate and evaporated to dryness. The residue is slurried in 400 ml of boiling methanol, cooled and filtered to yield 28 gms (89% theory) of product. Melting point 214°–215° C.

Analysis: Calc. For $C_{12}H_9Cl_2NO_3S$. C, 45.32; H, 2.83; N, 4.40. Found C, 45.67; H, 2.89; N, 4.55.

EXAMPLE 6

Preparation of 2-[2,5-Dimethylphenyl)methylsulfinyl]-3-methylpyridine N-oxide (Compound 70)

The thio compound described in U.S. Pat. No. 4,394,155, Example 2 (0.03 mol) is oxidized with MCPBA (0.03 mol) in 100 mL chloroform. After 24 hours at room temperature the chloroform solution is treated as described in U.S. Pat. No. 4,394,155, Example 1, yielding 5.5 g (66.6% yield) of a white solid m.p. 143°–145° C. from ethyl acetate. I.R. NO 1230 $cm^{-1}$, SO 1055 $cm^{-1}$.

| Elemental analysis: $C_{15}H_{17}NO_2S$ | | | | |
| --- | --- | --- | --- | --- |
| | C | H | N | S |
| Calculated: | 65.42 | 6.22 | 5.09 | 11.62 |
| Found: | 65.32 | 6.13 | 5.08 | 11.94 |

EXAMPLE 7

Preparation of 2-[1-(2,5-Dimethylphenyl)ethylsulfonyl]-3-methylpyridine N-oxide (Compound 71)

To a stirred suspension of 3 g (0.01 mol) of sulfone (described in U.S. Pat. No. 4,394,155, Example 2) in 15 mL of dry dimethylformamide cooled in an ice bath, is added 0.5 g sodium hydroxide powder. To this mixture is slowly added 0.75 mL methyl iodide. The reaction mixture is warmed to room temperature and stirred for 2 hours. 100 mL ice-water is slowly added with stirring. After filtration the white solid is recrystallized from toluene. Melting point: 146°–147° C. Structure confirmed by NMR. I.R. NO 1250 $cm^{-1}$, $SO_2$ 1350, 1140 $cm^{-1}$.

EXAMPLE 8

Preparation of
2-(2,3,6-Trimethylphenylmethylsulfinyl)pyridine
N-oxide (Compound 97)

The intermediate 2-(2,3,6-trimethylphenylmethylthio)pyridine N-oxide is prepared from α-2-bromoprehnitene with 2-mercaptopyridine N-oxide, sodium salt by a procedure similar to that described in U.S. Pat. No. 3,960,542, Example 2 for the preparation of the 2,4,6-trimethylphenyl isomer. Yield 50% theory. Melting point 108°–110° C. Structure confirmed by IR and NMR.

The thio compound (0.03 mole) is oxidized with MCPBA (0.03 mole) and isolated in the manner described in U.S. Pat. No. 3,960,542, Example 2. Yield 50% theory. Melting point 72°–75° C. (IR N→O 1250 $cm^{-1}$, SO 1050 $cm^{-1}$).

EXAMPLE 9

Preparation of 2-(1-Phenylethylsulfinyl)pyridine
N-oxide (Compound 102)

To a mixture of 23.2 g (0.1 mole) of 2-(1-phenylethylthio) pyridine N-oxide, 0.2 g of sodium tungstate, and 60 ml of glacial acetic acid were added 10 ml (0.1 mole) of 30% hydrogen peroxide over approximately 0.5 hours. The mixture exothermed somewhat to about 65° C. After completion of the reaction, the reaction mixture was poured slowly into 800 ml of vigorously stirred cold water. A solid separated out and was filtered off and washed with 15 ml of cold ethanol. The solid was air dried, melting point 130–130.5° C. Yield 14.5 g or 59%. An infrared spectrum confirmed the structure.

EXAMPLE 10

Preparation of 2-(alpha-phenyl-alpha-chloromethylsulfonyl)pyridine-N-oxide (Compound 105)

Carbon tetrachloride (3.1 g, 20 mmol) and freshly ground sodium hydroxide (1.0 g, 25 mmol) were placed in 25 ml of dimethylformamide. The mixture was cooled to 0° C. using an acetone-ice bath and while vigorously stirring, 2-(phenylmethylsulfonyl)pyridine-N-oxide (5.00 g, 20 mmol) was added in one portion. After 20 min, the mixture was poured into 300 ml of well-stirred water, resulting in a suspension of light tan precipitate.

The precipitate was filtered off, washed with excess water and air-dried to give 4.9 g of crude product (via NMR, 86% yield). Recrystallization from ethanol afforded a tan solid, m.p. 149°–150° C. (decomposed).

Analysis: Calc. For $C_{12}H_{10}ClNO_3S$: C: 50.79; H: 3.53; N: 4.94. Found: C: 50.77;H: 3.53; N: 4.82.

EXAMPLE 11

Preparation of 2-((2,5-dimethylphenyl)chloromethylsulphonyl)pyridine (Compound 106)

A mixture of 2.0 g (0.0064 mole) of 2-[[2,5-dimethylphenyl]chloromethylsulphonyl]pyridine-1-oxide (U.S. Pat. No. 4,360,677, Example 2), 3.5 g (0.026 mole) of phosphorus trichloride, and 15 ml of chloroform is refluxed for one-hour. Ethanol is then added to destroy excess phosphorus trichloride. The solvents were evaporated to give 2.6 g of crude product. One recrystallization of the crude product from ethanol gave 1.5 g of pure material m.p. 117–119° C. The material was identified as 2-((2,5-dimethylphenyl)chloromethylsulfonyl)pyridine by IR and NMR. Calculated for $C_{14}H_{14}ClNO_2S$: C:56.85, H:4.77, N:4.74. Found: C:56.67; H:4.78; N:4.81.

EXAMPLE 12

Preparation of 2-[1-(2,5-Dimethylphenyl)ethylsulfonyl]-4-methylpyridine N-oxide (Compound 108)

The intermediate 2-[1-(2,5-dimethylphenyl)ethylthio]-4-methylpyridine N-oxide is prepared from 2-(ethyl-1-thiol)-1,4-dimethylbenzene and 2-bromo-4-methylpyridine N-oxide hydrochloride by the procedure described in U.S. Pat. No. 4,394,155, Example 1. m.p. 130°–132° C. Structure is confirmed by analysis and I.R. Yield 98%.

The thio compound (0.07 mol) is oxidized in the manner described in U.S. Pat. No. 4,394,155, Example 1. Yield 79%. Melting point 204°–205° C. (I.R. NO 1240 cm$^{-1}$, SO$_2$ 1140, 1370 cm$^{-1}$).

Elemental analysis: $C_{16}H_{19}NO_3S$

|  | C | H | N | S |
|---|---|---|---|---|
| Calculated: | 62.92 | 6.27 | 4.58 | 10.50 |
| Found: | 61.79 | 6.20 | 4.51 | 10.19 |

EXAMPLE 13

Preparation of 2-[1-(2,5-Dimethylphenyl)ethylsulfonyl]-5-methylpyridine N-oxide (Compound 110)

Under a constant flow of nitrogen 3.32 g (0.02 mol) 2-(ethyl-1-thiol)-1,4-dimethylbenzene dissolved in 75 mL methanol is treated with 4.8 g (0.022 mol) 25% sodium methoxide in 75 mL methanol. To this stirred mixture is added 4.4 g (0.02 mol) 2-bromo-5-methylpyridine N-oxide hydrochloride which has previously been treated with 4.8 g (0.022 mol) sodium methoxide (25% in methanol). The reaction mixture is allowed to reflux for 1 hour, cooled and poured into 200 mL ice water. The white product is filtered off and air dried; yield 4.5 g (83%). Recrystallization from ethanol produces 2-[1-(2,5-dimethylphenyl)ethylthio]-5-methylpyridine N-oxide, m.p. 146°–148° C. Structure is confirmed by analysis and I.R.

To a stirred solution of 2.85 g (0.01 mol) of the sulfide compound in 50 mL chloroform at 5°–10° C. is added, with stirring, 4.6 g (0.024 mol) MCPBA in 175 mL chloroform. Upon completion of the addition, the reaction mixture is stirred at room temperature for two days then washed thoroughly with 150 mL saturated aqueous sodium bicarbonate, and dried over anhydrous magnesium sulfate. Evaporation of the chloroform, and crystallization of the solid residue from ethanol yields 2.6 g (82% of theory) of product. m.p. 143°–146° C. (I.R. NO 1280 cm$^{-1}$, SO$_2$ 1140, 1310 cm$^{-1}$).

Elemental analysis: $C_{16}H_{19}NO_3S$

|  | C | H | N | S |
|---|---|---|---|---|
| Calculated: | 62.92 | 6.27 | 4.58 | 10.50 |
| Found: | 62.56 | 6.09 | 4.52 | 10.25 |

EXAMPLE 14

Preparation of 2-(Phenylchloromethylsulfonyl)-5-chloropyridine N-oxide (Compound 114)

As described in U.S. Pat. No. 4,394,155, Example 1, 2-(phenylmethylthio)-5-chloropyridine N-oxide is prepared from 5-chloropyridine N-oxide and benzylmercaptan. To a well stirred solution of 2.5 g (9.01 mol) of the thio compound in 25 mL chloroform is added 4 g (0.02 mol) of MCPBA in 50 mL chloroform.

The sulfone is dissolved in DMF (20 mL) containing 0.25 g powdered sodium hydroxide and 1.5 g carbon tetrachloride at 0° C. The mixture is maintained at 0° C. for 20 minutes then poured in 200 mL water. The solid was filtered and dried. The product (0.55 g) m.p. 178°–179° C. (decomposed) is identified by I.R., NMR and mass spectographic analysis.

Elemental analysis: $C_{12}H_{11}NO_3ClS$

|  | C | H | N |
|---|---|---|---|
| Calculated: | 45.30 | 2.85 | 4.40 |
| Found: | 44.08 | 2.87 | 4.39 |

EXAMPLE 15

Preparation of 3-Chloro-2-[[(2,5-dimethylphenyl)methyl]thio]pyridine 1-oxide (Compound 133)

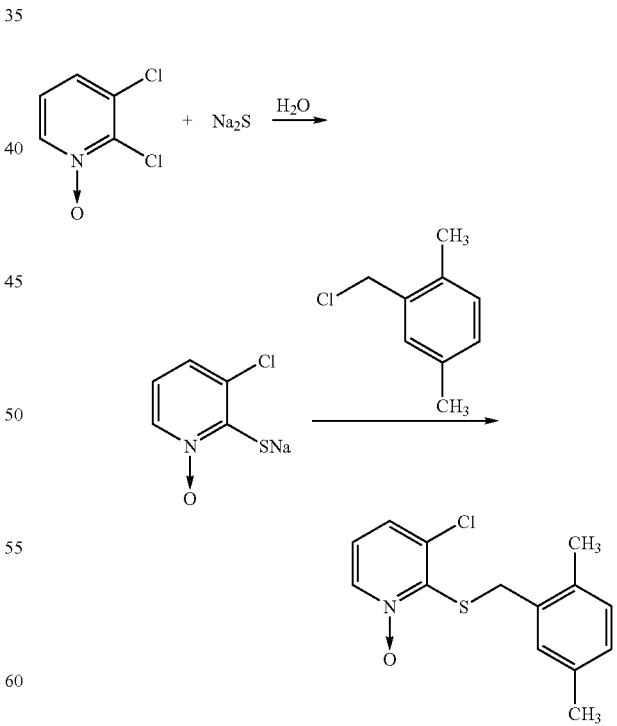

2,3-Dichloropyridine N-oxide (4.3 g, 0.026 mole) (prepared according to U.S. Pat. No. 3,850,939) and sodium sulfide (3.4 g, 0.026 mole) were mixed with 25 mL of water then heated to 70° C. for two hours. The resulting mixture was cooled to room temperature and treated with 2,5-dimethylbenzyl chloride (4.3 g, 0.026 mole) drop wise. After the addition, the mixture was heated to 70° C. for four hours, then cooled in an ice bath. The precipitated solid was filtered and washed with cold toluene leaving 3.5 g of product. Recrystallization from toluene afforded pure product of m.p. 77–80° C. The compound was identified by its NMR spectrum.

NMR data (CDC13): 2.3 (s, 6H); 4.5 (s, 2H); 7.1–8.0 (m, 6 H)

EXAMPLE 16

Preparation of 2-[(4-Methoxyphenyl)methylsulfonyl)]-4-(1,1-dimethylethyl)pyridine N-oxide (Compound 135)

Under nitrogen blanket 0.02 mol 4-methoxybenzylmercaptan is dissolved in 50 mL methanol and is treated with 0.022 mol sodium methoxide (25% in methanol). 2-Bromo-4-t-butylpyridine N-oxide hydrochloride (0.022 mol, previously treated with 0.22 mol sodium methoxide (25% in methanol)) is added with stirring. After ca. 1.5 hours at reflux, the reaction mixture is cooled and poured into 250 mL ice water. After filtration, the product, 2-[(4-methoxyphenylmethylthio]-4-(1,1-dimethylethyl)pyridine N-oxide, is recrystallized from ethanol. This product is converted to the corresponding sulfonyl compound following essentially the procedure of U.S. Pat. No. 4,394,155, Example 3.

EXAMPLE 17

Preparation of 2-[(Phenylmethyl)thio]-3-pyridinol (Compound 140)

To a mixture of 10.0 g of 2-mercapto-3-pyridinol, 11.0 g of potassium carbonate and 100 mL of 2-butanone was added dropwise with stirring, 13.3 g of benzyl bromide. After stirring at 22° C. for two hours, the mixture was heated to reflux for thirty minutes. The reaction mixture was concentrated under reduced pressure, the residue treated with water, and the mixture brought to pH 6 by the addition of acetic acid. The crude product was filtered and recrystallized from toluene to give 11.1 g of the title compound as a grey crystalline solid, mp 103–104° C. The structure of the product was confirmed by its $^1$H nmr and mass spectra.

EXAMPLE 18

Preparation of 2-((2,5-dimethylphenyl)methylthio)pyridine (Compound 148)

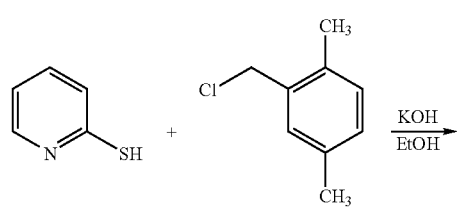

-continued

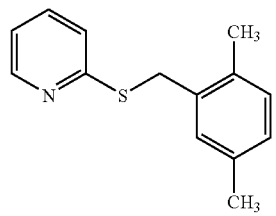

A mixture of 5.6 g (0.05 mole) of 2-mercaptopyridine, 3.3 g (0.05 mole) of potassium hydroxide (85% pellets), 35 ml of ethanol and 5 ml of water was prepared. To this mixture was added 7.8 g (0.05 mole) of 2,5-dimethyl-benzylchloride, while maintaining good stirring. The mixture was stirred and heated to 40° C. for 45 minutes, cooled to room temperature, and then added to 150 ml of water. The aqueous mixture was extracted with 150 ml of diethyl ether; the ether phase washed with 150 ml of water. Finally, the ether phase was dried with anhydrous sodium sulfate. Removal of the ether left a green oil.

An infrared spectrum was consistent with the structure of 2-((2,5-dimethylphenyl)methylthio) pyridine.

EXAMPLE 19

Preparation of 2-(((4-(1,1-dimethyl)propyl)phenyl)methylsulfonyl)pyridine-N-oxide (Compound 40)

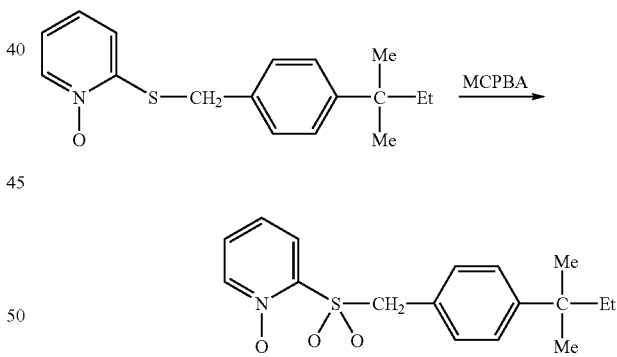

A mixture of 2.9 g (0.01 mole) of 2-(((4-(1,1dimethyl)propyl)phenyl)-methylthio)pyridine-N-oxide with 50 ml of chloroform and 80 ml of pH 7.5 phosphate buffer was maintained at 40° C. while 4 g (0.02 mole) of 85% metachloroperbenzoic acid (MCPBA) dissolved in 50 ml of chloroform was added. The mixture was stirred overnight, and the chloroform phase was then separated, washed with sodium bicarbonate, decanted and dried over anhydrous Na$_2$SO$_4$. The chloroform was filtered from the Na$_2$SO$_4$ and evaporated to leave 2.5 g of an oil which did not crystallize. An infrared spectrum was consistent with the structure.

EXAMPLE 20

Preparation of 2[1(9-anthryl)methylsulfonyl]pyridine-N-oxide (Compound 51)

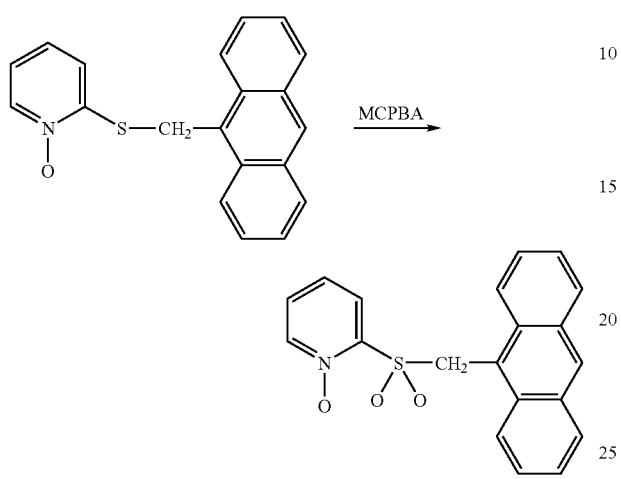

A mixture of 14.27 g (0.045 mole) of 2[1(9-anthryl)methylthio]-pyridine-N-oxide in 250 ml of chloroform was cooled to 10° C. and stirred. Then, 18 g (0.09 mole) of metachloroperbenzoic acid dissolved in 250 ml of chloroform was added slowly, and the reaction mixture was allowed to warm to room temperature and held at that temperature overnight. The reaction mixture was washed with NaHCO$_3$ solution in water, the chloroform layer was separated, and then dried with anhydrous sodium sulfate. The chloroform solution was filtered and the solvent removed. The residue was recrystallized from ethanol to give 10 g (66%) of a solid, melting point 213–215° C. Calculated for C$_{20}$H$_{15}$N$_3$S: C=68.76; H=4.33; N=4.01. Found: C=67.32; H=4.25; N=3.89.

EXAMPLE 21

Preparation of 2-[[(4-chloro-3-nitrophenyl)methyl]sulfonyl]-pyridine-1-oxide (Compound 64)

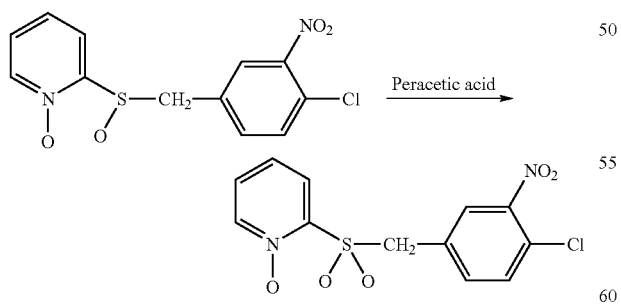

To a mixture of 14.0 g (0.0426 mole) of 2-[[(4-chloro-3-nitrophenyl)methyl]sulfinyl]-pyridine-N-oxide in 35 ml of acetic acid was added 10.1 g of peracetic acid (40% in acetic acid) dropwise over one hour. The temperature of the reaction mixture rose to 27° C. before a water bath was placed on the flask to hold the temperature at 25° C. After addition, the mixture was heated to 70° C. for five hours. The mixture was cooled, and 20 ml additional acetic acid and solid sodium bisulfate and water were added to destroy the excess peracetic acid. The aqueous mixture was neutralized with potassium carbonate and chilled in an ice bath to precipitate an almost white solid. The precipitate was filtered off, washed with water, dried under vacuum overnight, and found to have a melting point of 162–164° C. Infrared and NMR spectra were both consistent with the proposed structure. The product was recrystallized from ethanol to give needle-like white crystals, melting point 168–170° C. C,H,N calculated for C$_{12}$H$_9$ClN$_2$O$_5$S: C=43.85%; H=2.76%; N=8.52%. Found: C=43.27%; H=2.65%; N=8.21%

EXAMPLE 22

Preparation of 8-ethyl-4-methyl-2-[(1-phenylethyl)sulfonyl]-quinoline (Compound 107)

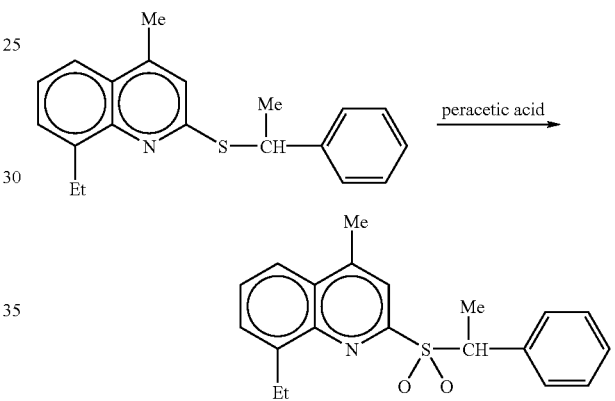

To a mixture of 4.5 g of 8-ethyl-4-methyl-2-[(1-phenylethyl)thio]-quinoline in 40 ml of acetic acid were added slowly 17.3 g of 40% peracetic acid in acetic acid. The mixture was stirred for three hours in an ice bath, brought to room temperature, and then stirred at room temperature overnight. A white precipitate formed, which was filtered off and recrystallized from ethanol, having a melting point of 146.5–147.5° C. Yield 2.7 g. NMR supported the structure. C,H,N,S calculated for C$_{22}$H25NO$_2$S: Theoretical: C=71.91; H=6.86; N=3.81; S=8.73; Found: C=71.73; H=7.00; N=3.53; S=6.46.

EXAMPLE 23

Preparation of 2-[[1-(2,5dimethylphenyl)ethyl]thio]-4-methyl-Quinoline (Compound 162)

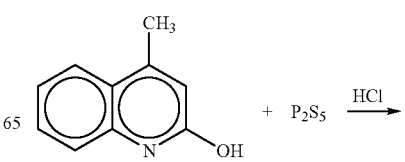

-continued

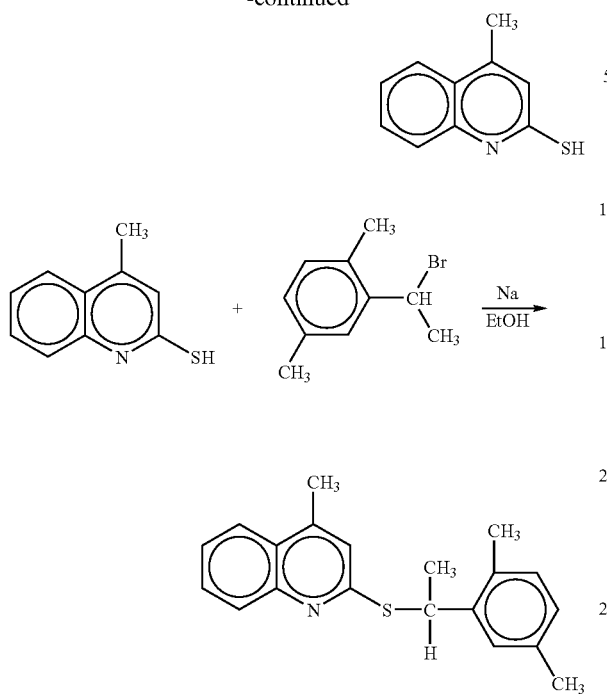

a) Preparation of 2-thiol-4-methylquinoline(Starting Material)

A mixture of 15.9 g of 2-hydroxy-4-methylquinoline and 24.4 g of $P_2S_5$ were heated together in an oil bath at 150° C. to give a homogeneous melt. The melt was cooled and then 100 ml of hydrochloric acid (90 ml of concentrated HCl and 10 ml of 10% HCl) were added and the mixture was refluxed for two hours. The mixture was then filtered hot through a large buchner funnel using coarse filter paper. The yellow/orange solid was dried in a vacuum oven, having a melting point of 250–253° C. NMR indicated that it was the desired thiol.

b) Preparation of 2-[[1-(2,5dimethylphenyl)ethyl]thio]-4-methyl-Quinoline

Sodium (1.2 g) was dissolved in 50 ml of ethanol and then 9.5 g of 2-thiol-4-methylquinoline (prepared in accordance with step (a) above), and 11.6 g of 2,5-dimethylphenyl(2-bromoethyl)benzene were added while stirring. An additional 50 ml of ethanol were then added and the reaction mixture was heated on a steam bath for five minutes, and was then filtered hot to remove some light brown precipitate. A reddish precipitate deposited in the cooled filtrate. This was filtered off and then taken up in carbon tetrachloride and water to remove sodium bromide. There was some material that was insoluble in both the organic and the water layer, and this was removed by filtration. The layers were separated and the carbon tetrachloride removed from the organic layer. The residue was crystallized from ethanol and then recrystallized from isopropanol, melting point 84–85° C. NMR was in agreement with the proposed structure. C,H,N calculated for $C_{20}H_{21}NS$: % C=78.14; % H=6.89; % N=4.56; Found: % C=78.13; % H=6.85; % N=4.46.

EXAMPLE 24

Preparation of 2-[((2,5-dimethylphenyl)methyl)sulfonyl]-3-methylpyridine-1-oxide (Compound

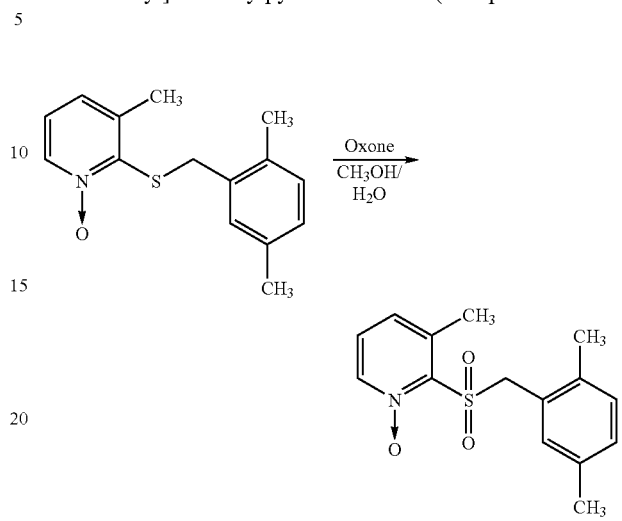

To a stirred solution of 4.0 g of 2-[((2,5-dimethylphenyl)methyl)thio]-3-methylpyridine-1-oxide in 50 mL of methanol, cooled to 3° C., was added a solution of 14.1 g of Oxone® in 50 mL of water over a period of 50 minutes. The reaction mixture was stirred at 24° C. overnight and then diluted with 200 mL of water. The product was extracted into chloroform and dried over magnesium sulfate. Evaporation of solvent under reduced pressure gave 4.1 g of 2-[((2,5-dimethylphenyl)methyl)sulfonyl]-3-methylpyridine-1-oxide as a white crystalline solid, having a melting point of 171–173° C. The $^1$H NMR spectrum (CDCl$_3$) was in agreement with the expected structure.

EXAMPLE 25

Preparation of 2-(Benzylsulfinyl)-pyridine-N-oxide (Compound 5)

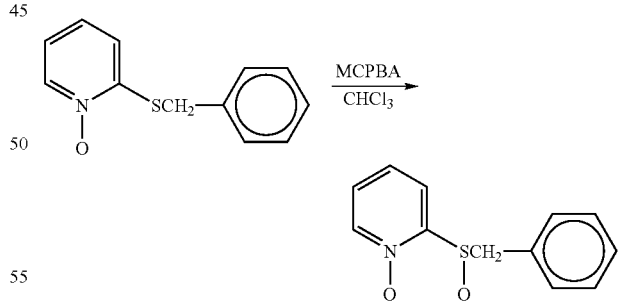

A mixture of 10.6 g (0.053 mole) of 2-(benzylthio)-pyridine-N-oxide and 50 ml of chloroform was cooled to less than 10° C. with stirring. A mixture of 10.6 g (0.05 mole) of metachloroperbenzoric acid (85%) in 50 ml of chloroform was then added dropwise to the above mixture. Stirring was continued for 6.5 hours at which time a TLC showed only one spot. Additional chloroform was added until the precipitate -had all dissolved. The chloroform solution was then washed with sodium bicarbonate, the layers separated, and the CHCl$_3$ layer dried with $N_{a2}SO_4$.

EXAMPLE 26

Preparation of 2-(Benzylsulfonyl)-pyridine-N-oxide (Compound 6)

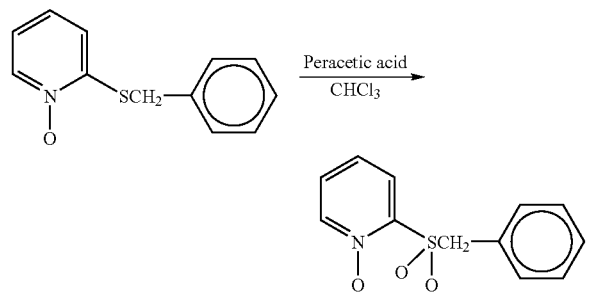

A mixture of 2.2 g (0.01 mole) of 2-(benzylthio)-pyridine-N-oxide, 50 ml of chloroform and 4 g of 40% peracetic acid in acetic acid was made and stirred at room temperature for 2.5 days. After this time, TLC indicated that the reaction was incomplete so the mixture was heated at 65° C. for two more days. TLC indicated the reaction to still be incomplete, so 2 ml of additional peracetic acid was added and heating continued for two more hours at which time a TLC showed only one spot. The mixture was cooled, washed with 50 ml of saturated $K_2CO_3$ solution, and the chloroform layer was dried over $Na_2SO_4$. The chloroform was removed to leave an oil which crystallized, melting point 127–128° C., yield 2.3 g. An infrared spectrum supported the proposed structure. See also Ann 695, 77 (1966).

EXAMPLE 27

Preparation of 2-(Pentachlorobenzylsulfonyl)-pyridine-N-oxide (Compound 32)

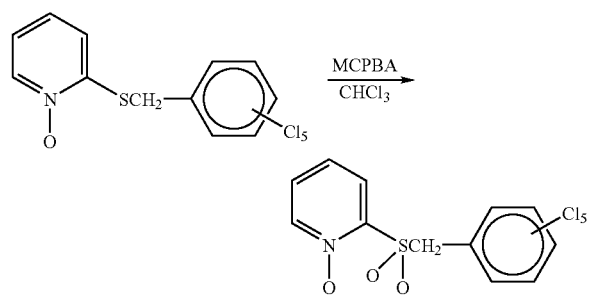

A solution of 8 g (0.04 mole) of metachloroperbenzoic acid (MCPBA), 85% purity, dissolved in 50 ml of chloroform was added to a stirred mixture of 2-(pentachlorobenzylthio)pyridine-N-oxide in 50 ml of chloroform while holding the mixture at 10° C. The mixture was stirred overnight at room temperature, and then washed with sodium bicarbonate solution. The chloroform layer was dried with sodium sulfate, filtered, and the chloroform removed. The residue was crystallized from ethanol, melting point 235–238° C., yield 7.1 g. An infrared supported the structure.

EXAMPLE 28

Preparation of 2-(4-(2,2-dichlorocyclopropyl)phenyl)methylsulfonyl)-pyridine-N-oxide (Compound 45)

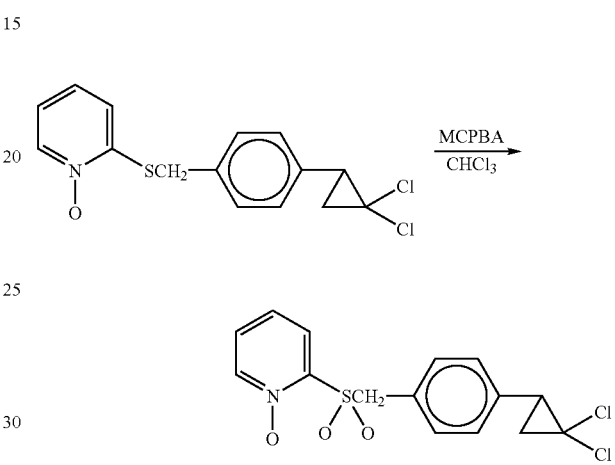

To a mixture of 9.8 g (0.03 mole) of 2-(4-(2,2-dichlorocyclopropyl)phenyl)-methylthio)-pyridine-N-oxide in 50 ml of chloroform were added with stirring at less than 10°C. a mixture of 12 g (0.06 mole) of metachloroperbenzoic acid (85%) in 75 ml of chloroform. The mixture was stirred overnight at room temperature. The mixture was then washed with saturated sodium bicarbonate solution and the chloroform layer was separated and then dried over sodium sulfate. The sodium sulfate was filtered off and the chloroform solution evaporated to leave an oily residue, yield 9.5 g. An infrared spectrum supported the proposed structure.

EXAMPLE 29

Preparation of 2-[(2,5-dimethylphenyl)chloromethylsulfonyl]-4-methylpyridine-1-oxide (Compound 74)

a) Preparation of 2-[(2,5-dimethylphenyl)methylthio]-4-methylpyridine-1-oxide

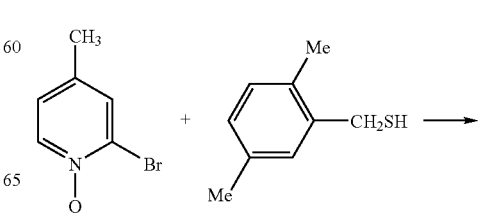

The dried $CHCl_3$ solution was evaporated to leave an oil which crystallized upon the addition of a little ethanol. The crystalline material was recrystallized from ethyl acetate, melting point 119–122° C., yield 7.6 g. An infrared spectrum supported the proposed structure.

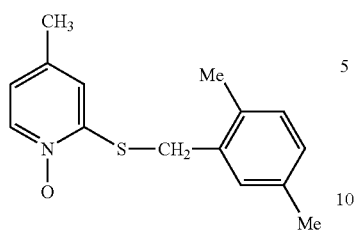

A mixture of 1.34 g (0.006 mole) of 2-bromo-4-methylpyridine hydrochloride, 1.06 g (0.007 mole) of 2,5-dimethylbenzylmercaptan and 0.56 g (0.014 mole) of powdered sodium hydroxide were stirred together at room temperature in 15 ml of DMF for 15 minutes. The reaction mixture was poured into water and the precipitate filtered off and washed with water. Yield 1.47 g or 95%.

b) Preparation of 2-[(2,5-dimethylphenyl)methylsulfonyl]-4-methylpyridine-1-oxide

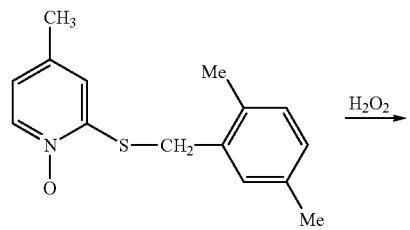

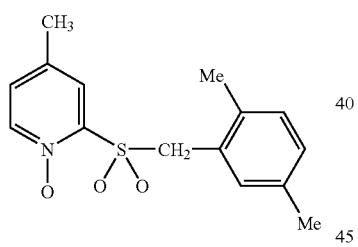

The sulfide isolated in step (a) above was dissolved in 20 ml of glacial acetic acid and 1.5 ml of 30% hydrogen peroxide was added along with 100 mg of sodium tungstate. The reaction mixture was heated at 40° C. for one hour, cooled, and poured into water to percipitate the product. Yield, 1.46 or 89%. NMR supported the proposed structure.

c) Preparation of 2-[(2,5-dimethylphenyl)chloromethylsulfonyl]-4-methyl-pyridine-1-oxide

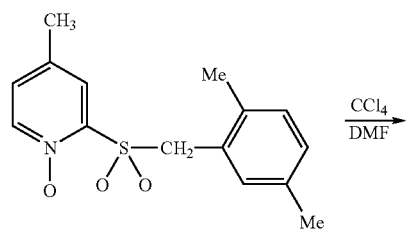

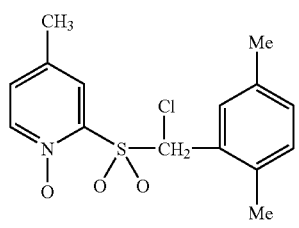

The sulfone (1.35 g or 0.0046 mole) prepared in step (b) above was added to a mixture of 0.20 g (0.005 mole) of sodium hydroxide, 1.5 g of carbon tetrachloride and 15 ml of DMF at 0° C. After 20 minutes of stirring, the reaction mixture was quenched with water and the precipitate was filtered off, washed with water, and dried. Yield, 1.26 g of crude material. The solid was recrystallized from a mixture of ethanol and chloroform to give 0.75 g of purified product, melting point 191° C. with decomposition. NMR supported the proposed structure.

EXAMPLE 30

Preparation of 2-(3,4-dichlorobenzylsulfonyl)-pyridine-N-oxide (Compound 37)

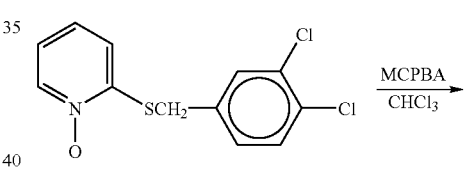

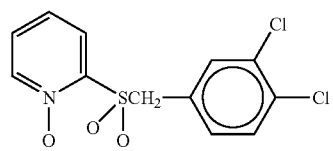

To a mixture of 11.4 g (0.04 mole) of 2-[(3,4-dichlorobenzylthio]-pyridine-N-oxide in 50 ml of chloroform were added with stirring at less than 10° C., a mixture of 16 g (0.08 mole) of metachloroperbenzoic acid (85%) in 100 ml of chloroform. The mixture was stirred overnight at room temperature. The mixture was then washed with saturated sodium bicarbonate solution, and the chloroform layer was separated and dried over sodium sulfate. The sodium sulfate was filtered off and the chloroform solution evaporated to leave a residue, which was crystallized from ethanol. The product was filtered off, and air-dried, melting point 170–173° C., yield 10 g. C, H, N, calculated for $C_{12}H_9NO_3SCl_2$: % C=45.30, % H=2.85; % N=4.40. Found: % C=45.10; % H=2.75; % N=4.49. An infrared spectrum supported the proposed structure.

EXAMPLE 31

Preparation of 2-(2,4,6-trimethylbenzylsulfinyl)-pyridine-N-oxide (Compound 88)

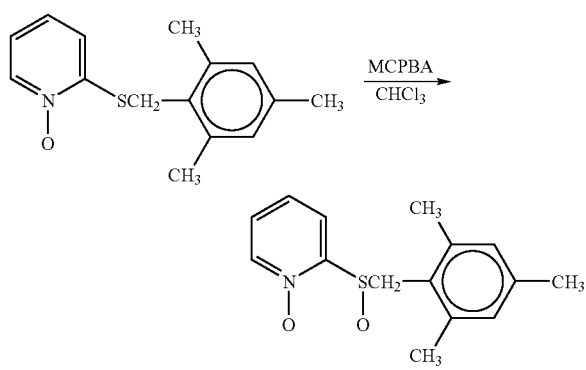

To a mixture of 7.8 g (0.03 mole) of 2-(2,4,6-trimethylbenzylthio)-pyridine-N-oxide in 50 ml of chloroform were added, with stirring at less than 10° C., a mixture of 6 g (0.03 mole) of metachloroperbenzoic acid (85%) in 100 ml of chloroform. The mixture was stirred overnight at room temperature. The mixture was then washed with saturated sodium bicarbonate solution, the chloroform layer was separated and dried over sodium sulfate. The sodium sulfate was filtered off and the chloroform solution evaporated to leave a residue, which was crystallized from ethanol. The product was filtered off, and air-dried, melting point 164–166° C., yield 7.2 g. C, H, N, calculated for $C_{15}H_{17}NO_2S$: % C=65.43; % H=6.22; % N=5.09. Found: % C=66.22; % H=6.63; % N=5.13.

EXAMPLE 32

Preparation of 2-[[1-(2,5-dimethylphenyl)propyl]sulfonyl]-3-methylpyridine-1-oxide (Compound 79)

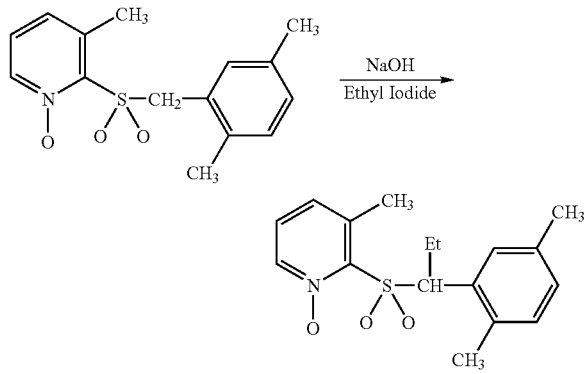

To a mixture of 5 g of 2-[[1-(2,5-dimethylphenyl)methyl]sulfonyl]-3-methylpyridine-1-oxide dissolved in 20 ml of dry dimethylformanide were added 0.8 g of sodium hydroxide. The mixture was cooled to 10° C. for 15 minutes and turned a red color. Then, 1.4 ml of ethyl iodide was added dropwise while maintaining the reaction mixture at 10° C. After addition, the mixture was allowed to warm and stir at room temperature for two hours. Ice water was then added to form a precipitate, 4.8 g which was recrystallized from toluene, melting point 160–165° C., 1.2 g. An nmr showed this to be starting material. The toluene filtrate was concentrated and ether was then added to precipitate the crude product, 2.3 g, melting point 118–128° C. The crude product was recrystallized from methanol and ether to give 1.2 g of purified product, melting point 124–129° C. NMR indicated that it was the desired product and a C,H,N analysis corresponded to the theoretical values for $C_{17}H_{21}NO_3S$.

EXAMPLE 33

Activity Against HIV

The cell type used to determine activity of the compounds of the invention herein, i.e., the test compounds, against HIV was human T-lymphoblast (CEM) cells obtained from the American Tissue Cell Culture Collection (Rockville, Md.). HIV-1 ($III_B$) was originally obtained from the culture of persistently HIV-1 infected H9 cells and was provided by R. C. Gallo and M. Popovic (National Cancer Institute, National Institutes of Health, Bethesda, Md.). HIV-2 (ROD) was originally obtained from L. M. Montagnier (Pasteur Institute, Paris, France).

To determine the antiviral activity of the test compounds, CEM cells were suspended at a cell density of approximately 300,000 cells per ml of culture medium and infected with approximately 100 $CCID_{50}$ (100 $CCID_{50}$ being the 50% cell culture infective dose) of HIV-1 (IIIB) or HIV-2 (ROD)). Then 100 µl of the infected cell suspensions was added to 200 µl micro titer plate wells containing 100 µl of appropriate serial (5-fold) dilutions of the test compounds. The inhibitory effect of the test compounds on HIV-1 or HIV-2 syncytium formation in CEM cells was examined microscopically on day four post infection. The 50% effective concentration ($EC_{50}$) was defined as the test compound concentration that inhibits syncytium formation in the HIV-1 or HIV-2 infected cell cultures by 50%.

In some cases, the compounds had considerable cytotoxicity to CEM cells which made determination of the $EC_{50}$ difficult. In these cases, the percent protection of the cells against virus-induced cytopathicity by the test compounds at the indicated compound concentration in the previous column is given.

The results are summarized in Table 3.

EXAMPLE 34

Activity Against HCMV

Confluent HEL cells grown in 96-cell microtiter plates were inoculated with CMV at an input of 100 PFU (plaque forming units) per well. After a one to two hour incubation period, residual virus was removed and the infected cells were further incubated with MEM (Minimal Essential Medium) (supplemented with 2% inactivated Fetal Calf Serum (FCS), 2 µM L-glutamine, and 0.3% sodium bicarbonate) containing varying concentrations of the test compounds. Antiviral activity was expressed as $EC_{50}$ (50% effective concentration), or test compound concentration required to reduce virus-induced cytopathicity after seven days by 50% compared to the untreated control.

In some cases, the compounds had considerable cytotoxicity against HEL cells, which made determination of the $EC_{50}$ difficult. In these cases, an estimate of the percent protection at the compound concentration indicated in the previous columns is given.

The results are summarized in Table 3.

EXAMPLE 35

Activity Against HHV-6

Two human immature T-lymphoblastoid cell lines were used: HSB-2, obtained from American Type Culture Collection (No. CCL 120.1); and MOLT-3, purchased from ABI Technologies (Columbia, Md., USA). The cells were propagated in RPMI 1640 medium supplemented with 10% fetal calf serum, 2 mM L-glutamine, 0.075% sodium bicarbonate and gentamycin. The cultures were incubated at 37° C. in a humidified and $CO_2$ controlled incubator.

The GS strain of HHV-6 variant A was kindly provided by Dr. R. Gallo, while the Z-29 strain of HHV-6 variant B was obtained from ABI Technologies (Columbia, Md., USA). For preparation of virus stocks, suspensions of HSB-2 cells infected with strain GS, or MOLT-3 cells infected with strain Z-29, were collected at 10–12 days post infection, when the cytopathic effect (CPE) was maximal and cells were >90% virus positive (as determined by immunofluorescence detection of HHV-6 antigens). Since the titer of virus released in culture supernatant was insufficient, virus stocks were used as whole cell suspensions, which were relatively stable when kept in aliquots at −80° C.

Stock solutions of the test compounds or of standards were prepared in dimethylsulfoxide or phosphate buffered saline (PBS). Working dilutions for the antiviral assays were prepared by appropriate dilution of the stock solutions in cell culture medium. The antiherpetic drug Foscarnet (PFA, Foscavir® from Astra, Södertälje, Sweden) was used as standard.

The antiviral assays were carried out as follows:

On day 0, the GS and Z-29 strains of HHV-6 were inoculated onto HSB-2 cells and MOLT-3 cells, respectively, at a multiplicity of infection of 0.001 $CCID_{50}$ (50% cell culture infective doses) per cell, and a cell suspension having a cell density of approximately $5 \times 10^6$ cells per ml of culture medium. After two hours of virus adsorption at 37° C., the unadsorbed virus was removed by centrifugation and the infected cells were resuspended and transferred to 48-well microtrays containing the test compounds or control in two- to five-fold dilutions. The final cell density of the suspended cells was approximately $0.8 \times 10^6$ cells per ml of culture medium.

The cells were incubated at 37° C. and subcultivated on days four and seven by two-fold dilution in medium containing fresh test compound or control. On days 10–14, the cells were examined microscopically to score the viral cytopathic effect (CPE) visible by the appearance of large ballooning cells and drug toxicity. Then total DNA was extracted from the infected cells with the QIAamp Blood Kit (Qiagen, Germany), using the manufacturer's instructions, and the DNA extracts were frozen at −20° C. until further analysis.

Viral DNA was detected by a slot blot assay as follows:

A digoxigenin labeled probe specific for strain GS or Z-29, was prepared by PCR reaction in the presence of digoxigenin-dUTP, on a 1-μl aliquot of a DNA extract prepared from infected cells showing manifest CPE. The 5'-3' primer sequence was GCTAGAACG TATTTGCTG-CAGAACG (Seq. Id. No. 1) and ATCCGAAACAACT-GTCTGACTGGCA (Seq. Id. No. 2), delimiting a 259 bp sequence within the U67 gene. The amplified product was separated on agarose gel and extracted from the gel fragment with the QIAquick gel extraction kit (Qiagen, Germany) after which the purified probe was frozen at −20° C.

For quantitation of viral DNA in the infected and drug-treated cell cultures, appropriate aliquots of the total DNA extracts (containing 5 μg of total DNA, as determined spectrophotometrically at 260 nm) were boiled during 10 min, and blotted on a nylon membrane (Hybond-N from Amersham) using a Hoefer slot blot apparatus from Pharmacia (Sweden). After UV cross-linking, the membrane was prehybridized during 30 min at 42° C. with DIG (digoxigenin) easy Hyb solution® (Boehringer Mannheim, Germany). Then, the GS- or Z-29 specific digoxigenin labeled probe was added and allowed to hybridize by incubation overnight at 42° C. After thorough washing (twice at room temperature in 2×SSC (sodium chloride/sodium citrate), 0.1% SDS (sodium dodecylsulfate) and twice at 65° C. in 0.1×SSC, 0.1% SDS), the membrane was treated with blocking reagent (Boehringer Mannheim, Germany). Then, the membrane was incubated for one hour with alkaline phosphatase-conjugated anti-digoxigenin antibody (Boehringer Mannheim, Germany) and after stringent washing, chemiluminescence detection was performed using CSPD (disodium 3-[4-methoxyspiro[1,2-dioxetane-3,2$^1$-(5-chloro) tricyclo[3,3,1,1,3,2]decan]-4-yl)phenylphosphate substrate from Clontech). After visualization on film, the intensity of the viral DNA bands was determined by densitometric scanning. The amounts of probe, anti-DIG antibody and CSPD substrate were standardized to ensure that the DNA band intensity was linear to the amount of viral DNA loaded on the membrane.

The antiviral $IC_{50}$ was calculated by extrapolation and defined as the compound concentration that produced 50% inhibition of virus replication as determined by microscopic examination or quantitation of viral DNA. Toxicity of the compounds was expressed as minimum cytotoxic concentration (MCC), or the lowest compound concentration that caused a microscopically visible alteration in cellular morphology.

The HHV-6 activity of some selected compounds of this invention and the PFA standard in MOLT-3 cells is shown in Table 4.

TABLE 3

| Compound No. | EC50 (ug/ml) HIV-1 | HIV-1 % Protection | EC50 (ug/ml) HIV-2 | HIV-2 % Protection | Antiviral EC50 (ug/ml) Davis strain CMV | Antiviral % Inhibition Davis strain CMV |
|---|---|---|---|---|---|---|
| 1 | 20.00 | | 41.0 | | >50 | 0.0 |
| 3 | 7.20 | | ≧20 | 37.5 | 36.0 | |
| 4 | ≧100 | 37.5 | >100 | 0.0 | >50 | 0.0 |
| 5 | 3.40 | | 2.1 | | >50 | 0.0 |
| 6 | 4.40 | | 4.4 | | 19.5 | |
| 7 | >.8 | 0.0 | >0.8 | 0.0 | 0.7 | |
| 8 | >20 | 0.0 | >20 | 0.0 | 11.0 | |

TABLE 3-continued

| Compound No. | EC50 (ug/ml) HIV-1 | HIV-1 % Protection | EC50 (ug/ml) HIV-2 | HIV-2 % Protection | Antiviral EC50 (ug/ml) Davis strain CMV | Antiviral % Inhibition Davis strain CMV |
| --- | --- | --- | --- | --- | --- | --- |
| 9 | ≧100 | 37.5 | >100 | 0.0 | >50 | 0.0 |
| 10 | 1.80 | | 5.8 | | 10.0 | |
| 11 | 13.00 | | 10.0 | | 29.0 | |
| 12 | 9.50 | | 9.5 | | 20.0 | |
| 13 | 6.50 | | 6.0 | | >5 | 20.0 |
| 14 | >4 | 0.0 | >4 | 25.0 | 7.0 | |
| 15 | 6.00 | | 7.0 | | 5.0 | |
| 16 | 11.00 | | 7.5 | | 12.0 | |
| 17 | 9.00 | | 8.0 | | 5.0 | |
| 18 | 2.40 | | 2.5 | | 5.0 | |
| 19 | ≧20 | 37.5 | 14.0 | | 20.0 | |
| 20 | 7.00 | | 13.0 | | 13.0 | |
| 21 | 11.70 | | 6.3 | | 10.0 | |
| 22 | 12.00 | | 6.3 | | 7.0 | |
| 23 | ≧20 | 37.5 | ≧20 | 37.5 | >20 | 20.0 |
| 24 | 7.00 | | 9.5 | | >5 | 30.0 |
| 25 | 10.00 | | ≧20 | 37.5 | 16.0 | |
| 27 | 2.40 | | 9.0 | | 16.0 | |
| 28 | 6.50 | | 7.5 | | >20 | 40.0 |
| 29 | 11.00 | | 7.0 | | >20 | 10.0 |
| 30 | 1.60 | | 14.0 | | 37.0 | |
| 31 | 4.00 | | 9.0 | | 10.0 | |
| 32 | 0.63 | | 1.0 | | 14.0 | |
| 33 | ≧4 | 37.5 | ≧4 | 37.5 | 5.0 | |
| 34 | 9.00 | | 10.0 | | >20 | 10.0 |
| 35 | ≧4 | 37.5 | ≧4 | 37.5 | 3.2 | |
| 37 | 1.00 | | 1.3 | | >5 | 30.0 |
| 38 | 2.50 | | ≧4 | 37.5 | 5.0 | |
| 39 | 9.00 | | J5.5 | | >20 | 30.0 |
| 40 | 3.10 | | 3.4 | | 1.5 | |
| 41 | 5.00 | | 4.7 | | 8.6 | |
| 42 | 8.00 | | ≧4 | 37.5 | >5 | 10.0 |
| 43 | ≧4 | 37.5 | ≧4 | 37.5 | >50 | 20.0 |
| 44 | 5.30 | | 3.4 | | >20 | 20.0 |
| 45 | 1.75 | | 1.5 | | 2.5 | |
| 46 | ≧20 | 37.5 | 15.0 | | >50 | 40.0 |
| 47 | 10.00 | | 35.0 | | >50 | 20.0 |
| 48 | 9.50 | | 16.0 | | >20 | 20.0 |
| 49 | ≧.8 | 37.5 | ≧.8 | 37.5 | 5.0 | |
| 50 | ≧20 | 37.5 | ≧20 | 37.5 | >50 | 20.0 |
| 51 | >.8 | 0.0 | >.8 | 0.0 | 1.3 | |
| 52 | 6.00 | | 6.5 | | 12.0 | |
| 53 | 2.33 | | 4.1 | | >5 | 20.0 |
| 54 | ≧4 | 37.5 | 4.0 | | 5.0 | |
| 55 | ≧4 | 37.5 | 2.6 | | 3.2 | |
| 56 | 5.30 | | 4.7 | | >5 | 20.0 |
| 58 | 3.40 | | 2.6 | | 5.0 | |
| 59 | 5.50 | | 5.0 | | 10.0 | |
| 60 | 40.00 | | 17.0 | | >50 | 0.0 |
| 61 | >4 | 0.0 | >4.0 | 6.0 | 14.0 | |
| 62 | 1.90 | | 5.0 | | >5 | 20.0 |
| 63 | 2.30 | | 2.5 | | 3.7 | |
| 64 | 1.50 | | 1.9 | | >5 | 10.0 |
| 65 | 2.80 | | 3.5 | | 5.0 | |
| 66 | 3.10 | | 2.5 | | 5.0 | |
| 67 | 2.30 | | 2.4 | | >50 | 20.0 |
| 69 | 2.90 | | 2.9 | | >5 | 20.0 |
| 70 | 12.00 | | ≧20 | 37.5 | 11.0 | |
| 71 | 0.05 | | >20.0 | 0.0 | 3.2 | |
| 72 | 4.00 | | >100.0 | 0.0 | >50 | 0.0 |
| 73 | 2.80 | | >100.0 | 0.0 | >20 | 40.0 |
| 74 | 0.42 | | >100.0 | 0.0 | 34.5 | |
| 76 | 0.90 | | 2.4 | | 9.1 | |
| 77 | 0.70 | | >0.8 | 0.0 | 11.0 | |
| 78 | 1.40 | | >100.0 | 0.0 | 10.0 | |
| 79 | 1.40 | | ≧20 | 37.5 | 0.8 | |
| 80 | 15.00 | | >20.0 | 0.0 | >20 | 0.0 |
| 81 | ≧20 | 37.5 | >20.0 | 0.0 | 8.6 | |
| 82 | 9.30 | | ≧20 | 37.5 | >5 | 0.0 |
| 83 | 6.00 | | ≧20 | 37.5 | 12.0 | |
| 85 | 13.00 | | 17.0 | | >50 | 20.0 |
| 86 | >.8 | 0.0 | >0.8 | 0.0 | 3.8 | |
| 88 | 1.50 | | 1.5 | | 25.0 | |
| 89 | 2.50 | | 2.8 | | 20.0 | |

TABLE 3-continued

| Compound No. | EC50 (ug/ml) HIV-1 | HIV-1 % Protection | EC50 (ug/ml) HIV-2 | HIV-2 % Protection | Antiviral EC50 (ug/ml) Davis strain CMV | Antiviral % Inhibition Davis strain CMV |
|---|---|---|---|---|---|---|
| 90 | ≧20 | 37.5 | | | 37.0 | |
| 91 | >4 | 0.0 | >4.0 | 0.0 | 34.5 | |
| 92 | ≧20 | 37.5 | 4.0 | | >50 | 10.0 |
| 93 | 8.00 | | ≧20 | 37.5 | >50 | 0.0 |
| 94 | 1.90 | | 2.6 | | 12.0 | |
| 95 | >4 | | ≧4 | 37.5 | 4.1 | |
| 96 | 20.00 | | 12.0 | | >50 | 0.0 |
| 97 | >.8 | 0.0 | >0.8 | 0.0 | 11.0 | |
| 98 | >.8 | 0.0 | >0.8 | 0.0 | 10.0 | |
| 102 | >.8 | 0.0 | >0.8 | 0.0 | 4.3 | |
| 103 | >.8 | 0.0 | >0.8 | 0.0 | 4.3 | |
| 104 | 40.00 | | 2.5 | | 34.5 | |
| 105 | 16.00 | | 2.5 | | 23.0 | |
| 106 | 0.90 | | >4.0 | 0.0 | 20.0 | |
| 107 | 0.65 | | >100 | | >20 | 0.0 |
| 108 | 0.75 | | ≧20 | 37.5 | 38.0 | |
| 110 | 5.50 | | >100.0 | 0.0 | 50.0 | |
| 114 | >.8 | 0.0 | >0.80 | 0.0 | >20 | 20.0 |
| 115 | >20 | 0.0 | >20.00 | 0.0 | >50 | 40.0 |
| 117 | 3.40 | | >4.0 | 0.0 | 12.0 | |
| 118 | >4 | | >4.0 | 0.0 | >5 | 10.0 |
| 120 | 3.30 | | >20.00 | 0.0 | 12.5 | |
| 121 | 11.00 | | 60.00 | | >50 | 0.0 |
| 123 | 60.00 | | >100 | 0.0 | >50 | 40.0 |
| 124 | >.8 | 0.0 | >0.80 | 0.0 | >5 | 10.0 |
| 125 | >4 | 0.0 | >4.0 | 0.0 | 31.5 | |
| 128 | ≧4 | 37.5 | 7.0 | | >20 | 40.0 |
| 129 | >14 | | 11.0 | | >5 | 20.0 |
| 132 | 2.40 | | >20.00 | 0.0 | >50 | 0.0 |
| 133 | 0.14 | | >20.00 | 0.0 | 25.0 | |
| 134 | >20 | 0.0 | >100.0 | 0.0 | 50.0 | |
| 135 | >20 | 0.0 | >20.00 | 0.0 | 12.5 | |
| 136 | 1.50 | | >4.0 | 0.0 | 4.7 | |
| 137 | >20 | 0.0 | >20.00 | 0.0 | 28.0 | |
| 138 | >100 | 0.0 | >100.0 | 0.0 | >50 | 20.0 |
| 139 | >20 | 0.0 | >20.00 | 0.0 | 43.0 | |
| 140 | 2.00 | | 12.0 | | 12.0 | |
| 142 | >4 | 0.0 | >4 | 0.0 | 3.4 | |
| 143 | 30.00 | | 50.0 | | >50 | 0.0 |
| 146 | 2.30 | | ≧20 | 37.5 | 40.0 | |
| 148 | >20 | | >20 | | 0.4 | |
| 149 | 9.00 | | 16.0 | | 20.0 | |
| 150 | 3.25 | | 20.0 | | >50 | 20.0 |
| 151 | >20 | 0.0 | >20.00 | 0.0 | >20 | 20.0 |
| 153 | 2.10 | | 3.0 | | 11.5 | |
| 156 | 16.00 | | >100 | 0.0 | >50 | 0.0 |
| 157 | 6.00 | | ≧20 | 37.5 | >50 | 0.0 |
| 158 | >4 | 0.0 | >4 | 0.0 | 3.6 | |
| 159 | >20 | 0.0 | >20 | 25.0 | 10.0 | |
| 160 | >20 | 0.0 | >20 | 0.0 | 7.0 | |
| 161 | 9.50 | | >100 | 0.0 | 38.0 | |
| 162 | >.8 | 0.0 | >.16 | 0.0 | 1.6 | |
| 163 | 3.25 | | >100 | 0.0 | >50 | 0.0 |
| 164 | 1.0 | | >20 | 0.0 | — | — |
| 165 | 0.14 | | >4 | 0.0 | — | — |
| DHPG | STANDARD FOR CMV | | | | 1 | |
| S-HPMPC | STANDARD FOR CMV | | | | 0.3 | |

TABLE 4

Anti-HHV-6 Activity in MOLT-3 Cells

| | $EC_{50}$ Based on $CPE^a$ (μg/ml) | | | $EC_{50}$ Based on Viral DMA Detection$^b$ (μg/ml) | | | $MIC^c$ (μg/ml) | | |
|---|---|---|---|---|---|---|---|---|---|
| Compound | Exp. 1 | Exp. 2 | Exp. 3 | Exp. 1 | Exp. 2 | Exp. 3 | Exp. 1 | Exp. 2 | Exp. 3 |
| PFA | 8.9 | 4.0 | 6.5 | 9.4 | 8.8 | 9.1 | >100 | >100 | >100 |
| Compound No. 5 | >100 | >200 | >100 | >100 | Nd | >100 | 100 | 100 | 100 |
| Compound No. 6 | 17.1 | 8.7 | 12.9 | 28.1 | 17.3 | 22.7 | 100 | 100 | 100 |
| Compound No. 10 | 12.6 | 11.1 | 11.8 | 21.8 | 9.4 | 15.6 | 50 | 100 | ≧50 |

$^a$Compound concentration that produces 50% inhibition of virus induced CPE (cytopathic effect) as determined by microscopic examination.
$^b$Compound concentration that produces 50% inhibition of virus replication as estimated from the intensity of the bands obtained after viral DNA detection.
$^c$Minimum inhibitory concentration or concentration causing minimal changes in cell morphology as determined by microscopic examination.
Data are the individual data from independent experiments.
Nd = Not done

What is claimed is:

1. A method of treating an infection by HCMV or HHV in an afflicted host which comprises administering to the host a therapeutically effective amount of a compound represented by the following formula:

A-L-B or a pharmaceutically acceptable acid-addition or base-addition salt thereof;

wherein:
component A is a functional group of the following formula:

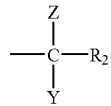

wherein Z is H, Cl, cyano, alkyl having from 1 to 15 carbon atoms, alkoxyalkyl having 2 or 3 carbon atoms; Y is H or a double bond to a carbon which is attached to R; and R is phenyl, biphenyl, benzyl, naphthyl, anthranyl, pyridyl, thienyl, quinolyl, isoquinolyl or phenyl substituted with 1 to 5 substituents which may be the same or different, the substituents being selected from the group consisting of lower alkyl having from 1 to 5 carbon atoms, halogen, nitro, methoxy, ethoxy, benzyloxy, methylenedioxy, 2,2-dichlorocyclopropyl, trifluoromethyl, methylsulfonyl, cyano and phenoxy;

component L is sulfonyl, sulfinyl or thio; and, component B is a functional group of the following formula:

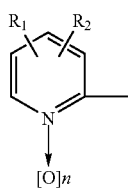

wherein n is 1, $R_1$ and $R_2$ may be the same or different and are H, halogen, lower alkyl having from 1 to 4 carbon atoms, hydroxy, or nitro.

2. The method of claim 1 wherein the infection being treated is an infection by HHV-6.

3. The method of claim 1 wherein the compound is selected from the group consisting of 2-(phenylmethylsulfonyl) pyridine-N-oxide, 2-[1-(2,5-dimethylphenyl)octylsulfonyl]pyridine-N-oxide, 2-[(2,5-dimethylphenyl)methylsulfonyl]pyridine-N-oxide, 2-[[1 -(2,5-dimethylphenyl)ethyl]sulfonyl]-3 -methylpyridine-N-oxide, 2-[[1-(2,5-dimethylphenyl)chloromethyl]sulfonyl]-4-methylpyridine-N-oxide, 2-[1-(2,5-dimethylphenyl)methylthio]-3-chloropyridine-N-oxide, 2-[(2,3,4,5,6-pentachlorophenyl)metheylsufonyl]pyridine N-oxide, 2[(3,4-dichlorophenyl)methylsulfonyl]pyridine-N-oxide, 2-[(4-(2,2-dichlorocyclopropyl)phenyl)methylsulfonyl]pyridine-N-oxide, 2-[(2,4,6-trimethylphenyl)methylsulfinyl]pyridine-N-oxide, 2-[(3-nitro-4-chlorophenyl)methylsulfonyl]pyridine-N-oxide, 2-[phenylmethylsulfinyl]pyridine-N-oxide, 2-[[1-(2,5-dimethylphenyl)propyl]sulfonyl]-3 -methylpyridine-N-oxide, 2-[(9-anthryl)methylsulfonyl]pyridine-N-oxide, 2-[4-((1,1 dimethyl)propyl) phenyl)methylsulfonyl]pyridine-N-oxide, 2-[[(2,5dimethylphenyl)methyl]sulfonyl]-3-methylpyridine-N-oxide and pharmaceutically acceptable acid-addition and base-addition salts thereof.

4. The method of claim 1 wherein the compound is contained in a composition containing a pharmaceutically acceptable carrier.

5. A method of inhibiting the replication of HCMV or HHV, the method comprising contacting the HCMV or HHV with an effective amount a compound represented by the following formula:

A-L-B or a pharmaceutically acceptable acid-addition or base-addition salt thereof;

wherein:

component A is a functional group of the following formula:

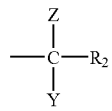

wherein Z is H, Cl, cyano, alkyl having from 1 to 15 carbon atoms, alkoxyalkyl having 2 or 3 carbon atoms; Y is H or a double bond to a carbon which is attached to R; and R is phenyl, biphenyl, benzyl, naphthyl, anthranyl, pyridyl, thienyl, quinolyl, isoquinolyl or phenyl substituted with 1 to 5 substituents which may be the same or different, the substituents being selected from the group consisting of lower alkyl having from 1 to 5 carbon atoms, halogen, nitro, methoxy, ethoxy, benzyloxy, methylenedioxy, 2,2-dichlorocyclopropyl, trifluoromethyl, methylsulfonyl, cyano and phenoxy;

component L is sulfonyl, sulfinyl or thio; and, component B is a functional group of the following formula:

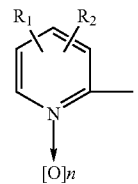

wherein n is 1, $R_1$ and $R_2$ may be the same or different and are H, halogen, lower alkyl having from 1 to 4 carbon atoms, hydroxy, or nitro.

6. The method of claim 5 wherein the HHV whose replication is being inhibited is HHV-6.

7. The method of claim 5 wherein the compound is selected from the group consisting of 2-(phenylmethylsulfonyl)pyridine-N-oxide, 2-[1-(2,5-dimethylphenyl)octylsulfonyl]pyridine-N-oxide, 2-[(2,5-dimethylphenyl)methylsulfonyl]pyridine-N-oxide, 2-[[1-(2,5-dimethylphenyl)ethyl]sulfonyl]-3-methylpyridine-N-oxide, 2-[[1-(2,5-dimethylphenyl)chloromethyl]sulfonyl]-4-methylpyridine-N-oxide, 2-[1-(2,5-dimethylphenyl)methylthio]-3-chloropyridine-N-oxide, 2-[(2,3,4,5,6-pentachlorophenyl)methylsulfonyl]pyridine N-oxide, 2-[(3,4-dichlorophenyl)methylsulfonyl]pyridine-N-oxide, 2-[(4-(2,2-dichlorocyclopropyl)phenyl)methylsulfonyl]pyridine-N-oxide, 2-[(2,4,6-trimethylphenyl)methylsulfinyl]pyridine-N-oxide, 2-[(3-nitro-4-chlorophenyl)methylsulfonyl]pyridine-N-oxide, 2-[phenylmethylsulfinyl]pyridine-N-oxide, 2-[[1-(2,5-dimethylphenyl)propyl]sulfonyl]-3-methylpyridine-N-oxide, 2-[(9-anthryl)methylsulfonyl]pyridine-N-oxide, 2-[4-((1,1dimethyl)propyl) phenyl)methylsulfonyl]pyridine-N-oxide, 2-[[(2,5dimethylphenyl)methyl]sulfonyl]-3-methylpyridine-N-oxide and pharmaceutically acceptable acid-addition and base-addition salts thereof.

8. The method of claim 5 wherein the compound is contained in a composition containing a pharmaceutically acceptable carrier.

9. A method of treating an HCMV infection in an afflicted host which comprises administering to the host a therapeutically effective amount of a compound selected from the group consisting of 2-[1-(2,5-dimethylphenyl)octylsulfonyl]pyridine-N-oxide, 2-[[1-(2,5-dimethylphenyl)propyl]sulfonyl]-3-methylpyridine-N-oxide, 2-[(9-anthryl)methylsulfonyl]pyridine-N-oxide, 2-[4-((1,1dimethyl)propyl)phenyl)methylsulfonyl]pyridine-N-oxide, and pharmaceutically acceptable acid-addition and base-addition salts thereof.

10. A method of treating an HHV-6 infection in an afflicted host which comprises administering to the host a therapeutically effective amount of a compound selected from the group consisting of 2-[(2,5-dimethylphenyl)methylsulfonyl]pyridine-N-oxide, and 2-(phenylmethylsulfonyl)pyridine-N-oxide and pharmaceutically acceptable acid-addition and base-addition salts thereof.

* * * * *